United States Patent
Emery

(10) Patent No.: US 10,154,819 B2
(45) Date of Patent: Dec. 18, 2018

(54) SYSTEMS AND METHODS FOR IMPEDANCE ANALYSIS OF CONDUCTIVE MEDIUM

(71) Applicant: Jack S. Emery, Davao (PH)

(72) Inventor: Jack S. Emery, Davao (PH)

(*) Notice: Subject to any disclaimer, the term of this patent is extended or adjusted under 35 U.S.C. 154(b) by 237 days.

(21) Appl. No.: 15/069,987

(22) Filed: Mar. 15, 2016

(65) Prior Publication Data

US 2016/0195484 A1    Jul. 7, 2016

Related U.S. Application Data

(60) Continuation-in-part of application No. 14/159,443, filed on Jan. 21, 2014, now Pat. No. 9,285,402, which is a continuation-in-part of application No. 13/223,265, filed on Aug. 31, 2011, now Pat. No. 8,633,710, which is a division of application No. 11/738,404, filed on Apr. 20, 2007, now Pat. No. 8,026,731.

(60) Provisional application No. 60/794,219, filed on Apr. 20, 2006.

(51) Int. Cl.
| | | |
|---|---|---|
| G01R 27/08 | (2006.01) | |
| G01N 27/02 | (2006.01) | |
| A61B 5/00 | (2006.01) | |
| A61B 5/053 | (2006.01) | |
| G01R 27/02 | (2006.01) | |
| G01R 27/14 | (2006.01) | |
| G01R 27/16 | (2006.01) | |
| G01R 19/00 | (2006.01) | |
| G01N 33/483 | (2006.01) | |

(52) U.S. Cl.
CPC .......... *A61B 5/7267* (2013.01); *A61B 5/0536* (2013.01); *G01R 19/0092* (2013.01); *G01R 27/02* (2013.01); *G01R 27/14* (2013.01); *G01R 27/16* (2013.01); *A61B 2576/00* (2013.01); *G01N 27/026* (2013.01); *G01N 33/4833* (2013.01); *G01R 19/0084* (2013.01); *G01R 27/08* (2013.01)

(58) Field of Classification Search
CPC .... G01R 27/00; G01R 27/0208; G01R 27/14; G01R 27/16; G01R 27/20; G01R 27/205; G01R 27/26; G01R 19/00; G01R 19/0084; G01R 19/0092; G01R 1/30; G01L 1/20; G01L 1/205; A61B 5/0536; A61B 5/7267; A61B 2576/00; G01N 27/026; G01N 33/4833
USPC .......... 324/600, 649, 691, 713, 76.11, 76.12, 324/76.19, 76.22, 430, 500, 512, 525, 324/756.06; 702/1, 57, 64, 65
See application file for complete search history.

(56) References Cited

U.S. PATENT DOCUMENTS

| | | | |
|---|---|---|---|
| 6,263,294 B1 * | 7/2001 | Frederickson | G01R 27/08 324/527 |
| 8,089,283 B2 * | 1/2012 | Kaplan | A61B 5/6843 324/525 |
| 2002/0106681 A1 * | 8/2002 | Wexler | A61B 5/0536 435/6.11 |

(Continued)

*Primary Examiner* — Hoai-An D Nguyen

(57) ABSTRACT

Systems and methods are disclosed for classifying a condition of an entity that includes a conductive medium having multiple conductive paths, using a pattern recognition strategy to classify a signature constructed from impedance-interrogation measurements and optionally including inputs from other informative sources which may be external to the system.

20 Claims, 13 Drawing Sheets

(56) References Cited

U.S. PATENT DOCUMENTS

| | | | |
|---|---|---|---|
| 2003/0216663 A1* | 11/2003 | Jersey-Willuhn | A61B 5/0536 600/547 |
| 2005/0179449 A1* | 8/2005 | Wooton | G01N 33/2888 324/691 |
| 2012/0041319 A1* | 2/2012 | Taylor | A61B 5/02007 600/508 |
| 2013/0002264 A1* | 1/2013 | Garber | A61B 5/0536 324/600 |

\* cited by examiner

SYSTEMS AND METHODS FOR IMPEDANCE ANALYSIS OF CONDUCTIVE MEDIUM

CROSS REFERENCE TO RELATED APPLICATION

This application is a continuation in part of U.S. application Ser. No. 14/159,443 entitled "Apparatus and Methods for Estimating Impedance in Conductive Medium," filed Jan. 21, 2014, issued as U.S. Pat. No. 9,285,402 as of Mar. 15, 2016, which is a continuation in part of U.S. application Ser. No. 13/223,265, entitled "Method and Apparatus For Constructing Images From Measurements of Impedance," filed Aug. 31, 2011, issued as U.S. Pat. No. 8,633,710 on Jan. 21, 2014, which is a division of U.S. application Ser. No. 11/738,404 of the same title, filed Apr. 20, 2007, issued Sep. 27, 2011, as U.S. Pat. No. 8,026,731, which claims the benefit of U.S. provisional application No. 60/794,219, filed Apr. 20, 2006; priority is claimed from all of the foregoing, and the contents thereof are incorporated herein by reference as though set forth in full.

STATEMENT REGARDING FEDERALLY SPONSORED RESEARCH

None

TECHNICAL FIELD

The present disclosure relates to the field of impedance measurement and electrical impedance imaging.

BACKGROUND

Disclosed herein are methods, devices, apparatus, and articles of manufacture relating to the measurement or estimation of impedance properties, and/or their spatial distribution, in a conductive continuous medium or other conductive system presenting multiple conductive paths. Among other applications, the methods, apparatus, and articles of manufacture disclosed herein are well-suited for use in electrical impedance imaging and electrical impedance spectroscopy applications.

Many investigators have attempted to devise methods for producing images corresponding to the electrical impedance properties of a two or three dimensional object based upon measurements taken from electrodes placed around the outside of (and/or, optionally, at selected points within) the object. Potential applications of such a technology (referred to as electrical impedance tomography, or 'EIT') include medical imaging and diagnosis, and geological profiling.

Previous approaches to the problem have typically involved passing currents between various pairs of electrodes arrayed around the periphery of the object to be imaged. Multiple frequencies may be employed, and/or currents may be passed through multiple electrodes at once. Thus far, however, there has been relatively little success in reconstructing meaningful and reproducible images at a useful resolution, because of a seemingly intractable problem: currents applied through electrodes follow multiple paths of least resistance that themselves depend on the impedance characteristics of the object and are therefore unpredictable. Because of this, impedance imaging is in principle unlike other kinds of imaging such as computed tomography, where the measured signal represents an integral of the property being measured (such as density to x-rays) along a straight line path, which allows for straightforward reconstruction of a unique image from a number of such measurements along a variety of paths. In computed tomography where the measured data consists of line integrals of some physical property, reconstruction is accomplished using techniques that are well known to persons having ordinary skill in the art of imaging, such as back projection or Fourier analysis. Because the measurements sought to be used for impedance imaging are not line integrals, but rather represent the effect of the impedance properties of the object to be imaged along many paths at once, the problem of reconstructing an image from impedance measurements (often referred to as the 'inverse EIT problem') is one of a class of inverse problems known to be highly nonlinear, extremely ill-posed, and having many local optima.

Previous efforts to obtain useful images despite these drawbacks have typically focused on seeking ways to make the reconstruction problem less intractable—for example, in physiological imaging, the analysis may begin with an assumed mapping of the typical impedance properties and topography of the anatomical region sought to be measured. It may then be possible to construct an image at some resolution by using the assumed mapping to predict the path distribution of the applied currents, and use the results of the measurements to iteratively improve the mapping.

The present disclosure takes a different approach: in some embodiments, it seeks to make measurements in such a way that the current along a path of interest between electrodes can be estimated, thereby providing line integrals or estimates thereof from which images can be reconstructed directly using any of the many well-known line integral-based image reconstruction methods. More generally, embodiments of methods and apparatus are disclosed for estimating spatially localized impedance properties along a conductive path of interest or in a localized region of interest, and embodiments of systems and methods are disclosed for classifying a condition of an entity using signatures of electrical properties.

SUMMARY

Disclosed herein are embodiments of systems and methods (and computing apparatus and measurement apparatus implementing such methods) for obtaining an image of impedance properties of an object from a plurality of current measurements made between combinations of electrodes placed at selected points, typically around the periphery of the object but also optionally within the interior of the object. The measurements in question are able, in embodiments, to estimate a measure of the impedance along a straight line path between electrodes by taking advantage of any of several novel strategies, which may be used individually or in combination, as described in detail infra: (1) the use of the phase shifts and current amplitudes measured at a plurality of frequencies, together with knowledge of the distance between electrodes, to determine the part of the current attenuation attributable to the straight line path, and/or (2) the use of a calibrated frequency to produce a standing wave along the straight line path, thereby, in effect, interrogating the straight line path with a signal that is resonant along that path, and/or (3) analysis of the signal produced in response to a step potential to estimate a shortest-path impedance property, and/or (4) the controlled induction of changes in the conductive properties of a localized region of interest in the conductive medium so that changes in conducted electrical currents can be correlated with the induced changes in properties and/or with the location of the changes. In embodiments, using these and/or other measurements relating to a conductive medium as disclosed herein, a signature may be obtained characterizing a condition of an entity that includes the conductive medium, and the condition may be classified.

It will be apparent to persons of skill in the art that various of the foregoing aspects and/or objects, and various other aspects and/or objects disclosed herein, can be incorporated and/or achieved separately or combined in a single device, method, composition, or article of manufacture, thus obtaining the benefit of more than one aspect and/or object, and that an embodiment may encompass none, one, or more than one but less than all of the aspects, objects, or features enumerated in the foregoing summary. The disclosure hereof extends to all such combinations. In addition to the illustrative aspects, embodiments, objects, and features described above, further aspects, embodiments, objects, and features will become apparent by reference to the drawings and detailed description. Also disclosed herein are various embodiments of related methods, devices, apparatus, and articles of manufacture. The foregoing summary is intended to provide a brief introduction to the subject matter of this disclosure and does not in any way limit or circumscribe the scope of the invention(s) disclosed herein, which scope is defined by the claims currently appended or as they may be amended, and as interpreted in the light of the entire disclosure.

BRIEF DESCRIPTION OF THE DRAWING FIGURES

Figures are not to scale unless expressly so labeled, and relative positions of objects and components are illustrative. Persons of skill in the art will recognize that many other arrangements, configurations, dimensions, and selections of components are possible and consistent with the disclosure hereof, and are in no way limited to the embodiments shown in the figures.

DETAILED DESCRIPTION

Disclosed herein are methods, apparatus, compositions, systems, and articles of manufacture useful for estimating impedance properties and their spatial relationships in a conductive medium that presents more than a single conductive path. In embodiments, for example, a two- or three-dimensional dimensional object may offer two or more conductive paths between selected points at the periphery or in the interior of the object, and an estimate may be made of an impedance property or measure thereof along a particular conductive path, or in a localized spatial region. In embodiments, from a plurality of such measurements, a spatial distribution of impedance properties may be estimated, and/or an image or plot may be produced. In embodiments, a signature characterizing a condition of an entity that includes the conductive medium may be obtained from a plurality of measurements, and the condition of the entity may be classified using the system and methods disclosed. In Part A are disclosed strategies and embodiments relating to estimating an impedance property along a straight-line path or shortest path. In Part B are disclosed strategies and embodiments relating to estimating an impedance property of a localized spatial region. In Part C are disclosed strategies and embodiments relating to the extraction of a signature and/or classification of a condition based on measurements.

A. Methods and Apparatus Relating to Estimation of Impedance of Straight Line or Shortest Path A motivation of the method and apparatus described here is to solve the problem of the fundamental intractability of the impedance imaging problem by obtaining measurements from which line integrals, or at least bounded estimates of line integrals, of impedance properties can be obtained. Current passed between electrodes follows multiple paths, and there is no known reliable technique for physically confining the electrical current to a predetermined path, so in order to obtain line integral measurements, it is necessary to devise a way of determining which part of the injected current did in fact follow the straight line path. The discussion to follow will describe a system and method for making that determination, involving several related techniques that can be used separately or together and that enable the embodiments disclosed herein.

Figure 1:
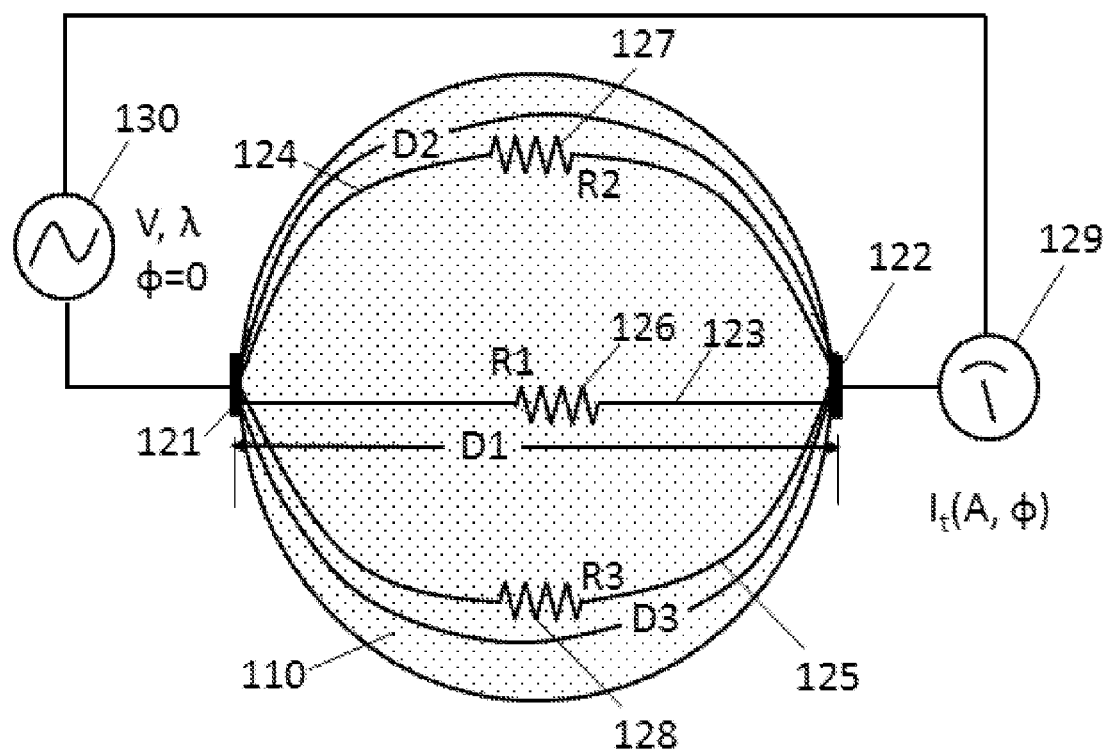
FIG. 1 illustrates the modeling of impedance properties of an object for computational purposes.

1. Determination of Line Integral Impedance Properties from Amplitude and Phase Shift Measurements at Multiple Frequencies Consider an alternating current signal of predetermined frequency, which may be applied from a signal source 130 between two electrodes 121, 122 placed on the periphery of an object to be imaged as shown in FIG. 1. The resistance properties of the object can be approximated by an array of parallel resistors $R_1$ 126, $R_2$ 127, and $R_3$ 128 as shown, each on a separate circuit branch 123, 124, 125 respectively, which branches are of length $D_1$, $D_2$, and $D_3$ respectively.

(The approximation can be improved using a larger number of parallel paths; in this illustration only three are shown, for simplicity. The system and method described is generalizable to any number of paths. Capacitance and inductance effects are also ignored in this example for simplicity, as are resonant effects; these will be discussed infra.) If a sinusoidal signal at a fixed frequency f and specified potential V (herein referred to as an "interrogation signal") is applied across the electrodes 121 and 122, alternating currents will be produced in each of the circuit branches 123, 124, 125, and these alternating currents will superpose at the 'downstream' electrode 122, producing a composite current signal, still of frequency f, but, in general, shifted in phase and attenuated in amplitude from the 'upstream' current at the electrode 121. This phase shift and attenuation occurs because all branches except the straight line path 123 are longer than the straight line path, so the signals on the non-straight line paths (hereinafter referred to as the shunt paths) are relatively delayed in their arrival at the 'downstream' electrode 122 by an amount of time that varies according to the ratio of the shunt path length to the straight line path length. Thus when the signals from the several branches superpose at the 'downstream' electrode, they interfere destructively to a greater or lesser degree, causing the downstream current to be attenuated and phase shifted. (This result may seem counterintuitive, since the usual principles of circuit analysis would require the 'upstream' current to equal the 'downstream' current. However, the usual principles of circuit analysis do not take into account propagation delay due to the differences in path length, since the attenuation and phase shift is negligible at the frequencies usually analyzed, which correspond to wavelengths that are large relative to the path lengths. Note: as used herein, two or more signals are said to interfere constructively if and only if they are in phase, so that the amplitude of the signal obtained by superposing them is equal to the sum of the amplitudes of the separate signals. They are said to interfere destructively if any of the signals being superposed is out of phase to any significant degree, in which case the amplitude of the signal obtained by superposing them will always be less than the sum of the amplitudes of the separate signals.)

The attenuation and phase shift caused by the interference of the signals traveling along the various paths can be used to infer the amplitude of the individual path currents, in the manner disclosed herein. In general, doing so requires knowledge of (1) the fixed potential of each applied interrogation signal, (2) the lengths of each of the current paths, and (3) the amplitude of the current at the 'downstream' electrode and the phase of that current relative to the applied signal or some other datum, with measurements taken at a number of fixed frequencies at least equal to the number of paths to be evaluated. The discussion to follow will first describe how this may be done in the context of the simplified model of FIG. 1, then discuss how the model may be generalized to the problem of estimating the impedance along straight line paths through two or three dimensional objects.

Consider an alternating current signal of fixed potential V and frequency $f_1$ applied across electrodes 121 and 122 in FIG. 1. A current $I_{1,1}$ will be produced in the straight line path 123 equal to $V/R_1$ and will be phase shifted relative to the applied signal by an angle in radians equal to $2\pi(D_1-\lambda_1)/\lambda_1$, where $\lambda_1$ is the wavelength corresponding to $f_1$ and given by $\lambda_1=c/f_1$, where c is the speed of propagation of an electromagnetic signal in the medium through which the current is passing. A current $I_{1,2}$ equal to $V/R_2$ will be produced in the shunt path 124, and will be phase shifted relative to $I_1$ by an amount equal to $2\pi(D_2-\lambda_1)/\lambda_1$. Similarly, A current $I_{1,3}$ equal to $V/R_3$ will be produced in the shunt path 125, and will be phase shifted relative to $I_1$ by an amount equal to $2\pi(D_3-\lambda_1)/\lambda_1$. (For consistency, a current $I_{x,y}$ will be taken throughout this written description to mean the current in branch y due to application of frequency $f_x$. A current $I_x$ will be taken to refer to the aggregate superposed current from all paths measured at the downstream electrode due to application of frequency $f_x$.)

It is convenient to represent these currents $I_{1,1}$, $I_{1,2}$, $I_{1,3}$ in complex form as $(V/R_1)\cos(2\pi(D_1-\lambda_1)/\lambda_1)+j((V/R_1)\sin(2\pi(D_2-\lambda_1)/\lambda_1))$, $(V/R_2)\cos(2\pi(D_2-\lambda_1)/\lambda_1)+j((V/R_2)\sin(2\pi(D_2-\lambda_1)/\lambda_1))$, and $(V/R_3)\cos(2\pi(D_3-\lambda_1)/\lambda_1)+j((V/R_3)\sin(2\pi(D_3-\lambda_1)/\lambda_1))$, respectively, where j is the square root of minus one. The measured total current $I_1$ obtained by employing a measuring instrument 129 to make a current measurement at the downstream electrode 122 after applying frequency $f_1$ will be given by the sum of these three complex values.

The analysis of the preceding two paragraphs can be repeated at two additional frequencies $f_2$ and $f_3$, corresponding to additional wavelengths $\lambda_2$ and $\lambda_3$, and giving branch currents in circuit branches 123, 124, 125 of $(V/R_1)\cos(2\pi(D_1-\lambda_2)/\lambda_2)+j((V/R_1)\sin(2\pi(D_2-\lambda_2)/\lambda_2))$, $(V/R_2)\cos(2\pi(D_2-\lambda_2)/\lambda_2)+j((V/R_2)\sin(2\pi(D_2-\lambda_2)/\lambda_2))$, and $(V/R_3)\cos(2\pi(D_3-\lambda_2)/\lambda_2)+j((V/R_3)\sin(2\pi(D_3-\lambda_2)/\lambda_2))$, respectively, when the signal at frequency $f_2$ is applied, and $(V/R_1)\cos(2\pi(D_1-\lambda_3)/\lambda_3)+j((V/R_1)\sin(2\pi(D_2-\lambda_3)/\lambda_3))$, $(V/R_2)\cos(2\pi(D_2-\lambda_3)/\lambda_3)+j((V/R_2)\sin(2\pi(D_2-\lambda_3)/\lambda_3))$, and $(V/R_3)\cos(2\pi(D_3-\lambda_3)/\lambda_3)+j((V/R_3)\sin(2\pi(D_3-\lambda_3)/\lambda_3))$, respectively, when the signal at frequency $f_3$ is applied. Again, the branch currents, expressed in complex form, may be summed to give the currents $I_2$ and $I_3$ that will be measured at the downstream electrode 122.

The relations described in the three preceding paragraphs comprise a linear system as follows:

$$\frac{I_1}{V} = \left(\frac{1}{R_1}\right)\left(\cos\left(2\pi\frac{(D_1-\lambda_1)}{\lambda_1}\right)+j\cdot\sin\left(2\pi\frac{(D_1-\lambda_1)}{\lambda_1}\right)\right)+$$
$$\left(\frac{1}{R_2}\right)\left(\cos\left(2\pi\frac{(D_2-\lambda_1)}{\lambda_1}\right)+j\cdot\sin\left(2\pi\frac{(D_2-\lambda_1)}{\lambda_1}\right)\right)+$$
$$\left(\frac{1}{R_3}\right)\left(\cos\left(2\pi\frac{(D_3-\lambda_1)}{\lambda_1}\right)+j\cdot\sin\left(2\pi\frac{(D_3-\lambda_1)}{\lambda_1}\right)\right),$$

$$\frac{I_2}{V} = \left(\frac{1}{R_1}\right)\left(\cos\left(2\pi\frac{(D_1-\lambda_2)}{\lambda_2}\right)+j\cdot\sin\left(2\pi\frac{(D_1-\lambda_2)}{\lambda_2}\right)\right)+$$
$$\left(\frac{1}{R_2}\right)\left(\cos\left(2\pi\frac{(D_2-\lambda_2)}{\lambda_2}\right)+j\cdot\sin\left(2\pi\frac{(D_2-\lambda_2)}{\lambda_2}\right)\right)+$$
$$\left(\frac{1}{R_3}\right)\left(\cos\left(2\pi\frac{(D_3-\lambda_2)}{\lambda_2}\right)+j\cdot\sin\left(2\pi\frac{(D_3-\lambda_2)}{\lambda_2}\right)\right),$$

$$\frac{I_3}{V} = \left(\frac{1}{R_1}\right)\left(\cos\left(2\pi\frac{(D_1-\lambda_3)}{\lambda_3}\right)+j\cdot\sin\left(2\pi\frac{(D_1-\lambda_3)}{\lambda_3}\right)\right)+$$
$$\left(\frac{1}{R_2}\right)\left(\cos\left(2\pi\frac{(D_2-\lambda_3)}{\lambda_3}\right)+j\cdot\sin\left(2\pi\frac{(D_2-\lambda_3)}{\lambda_3}\right)\right)+$$
$$\left(\frac{1}{R_3}\right)\left(\cos\left(2\pi\frac{(D_3-\lambda_3)}{\lambda_3}\right)+j\cdot\sin\left(2\pi\frac{(D_3-\lambda_3)}{\lambda_3}\right)\right)$$

The quantities $1/R_1$, $1/R_2$, $1/R_3$ may therefore be determined by solving the foregoing linear system, using any of the many techniques for solving linear systems that are known to persons having ordinary skill in the art of linear mathematics, such as, by way of example only, Gaussian elimination or matrix inversion. To do this it is merely necessary to know V, which in the case of actual physical measurement is known because it is the fixed voltage applied; $I_1$, $I_2$, and $I_3$, which are known by, for example, measuring the current amplitudes and phases directly using a suitable instrument 129 at the downstream electrode 122 upon applying frequencies corresponding to wavelengths $\lambda_1$, $\lambda_2$, and $\lambda_3$; the path lengths $D_1$, $D_2$, and $D_3$, which in this example are given and in the context of an actual measurement on an object could be determined, for example, by direct measurement of the straight line distance $D_1$ between electrodes and choosing suitable arbitrary values for $D_2$ and $D_3$ as described infra; and the wavelengths $\lambda_1$, $\lambda_2$, and $\lambda_3$, which may be determined from the known frequencies applied, assuming the speed of propagation in the medium is known (and if not it can be measured or estimated).

The linear system can be expressed in matrix form and generalized to any arbitrary number of resistance paths and interrogating signal wavelengths, as follows:

$$\left(\frac{I_n}{V_n}\right) = \left(\cos\left(2\pi\frac{(D_m - \lambda_n)}{\lambda_n}\right) + j \cdot \sin\left(2\pi\frac{(D_m - \lambda_n)}{\lambda_n}\right)\right)\left(\frac{1}{R_m}\right)$$

where $$\left(\frac{I_n}{V_n}\right)$$

is a column vector of n observed currents (scaled by the applied voltage amplitude, which can optionally be different for each frequency, hence the subscript), expressed in polar form, at the downstream electrode upon applying an alternating current at potential V and frequencies $f_1 \ldots f_n$ corresponding to wavelengths in the medium being interrogated of $\lambda_1 \ldots \lambda_n$;

$$\left(\frac{1}{R_m}\right)$$

is a column vector of the m resistances in paths 1 ... m; and $$\left(\cos\left(2\pi\frac{(D_m - \lambda_n)}{\lambda_n}\right) + j \cdot \sin\left(2\pi\frac{(D_m - \lambda_n)}{\lambda_n}\right)\right)$$

is a n (rows) by m (columns) matrix of coefficients corresponding to the phase shift attributable to the difference between the path length along path m and the wavelength $\lambda_n$ of the applied signal. The number of different interrogating frequencies n should preferably be chosen to be at least equal to the number of paths to be evaluated m; if the number of frequencies n is less than the number of paths m, the system will in general be underdetermined, and if the number of frequencies n exceeds the number of paths m, the system will in general be overdetermined. In the latter case, use may be made of various techniques known to persons having ordinary skill in the art of linear mathematics for improving the accuracy of the solution by utilizing the additional information embodied in the constraints exceeding the number of degrees of freedom of the system. In the former case, techniques familiar to persons of skill in the art may be employed to estimate a solution from the underdetermined system.

Extending the Model to Account for Capacitance

Figure 2:
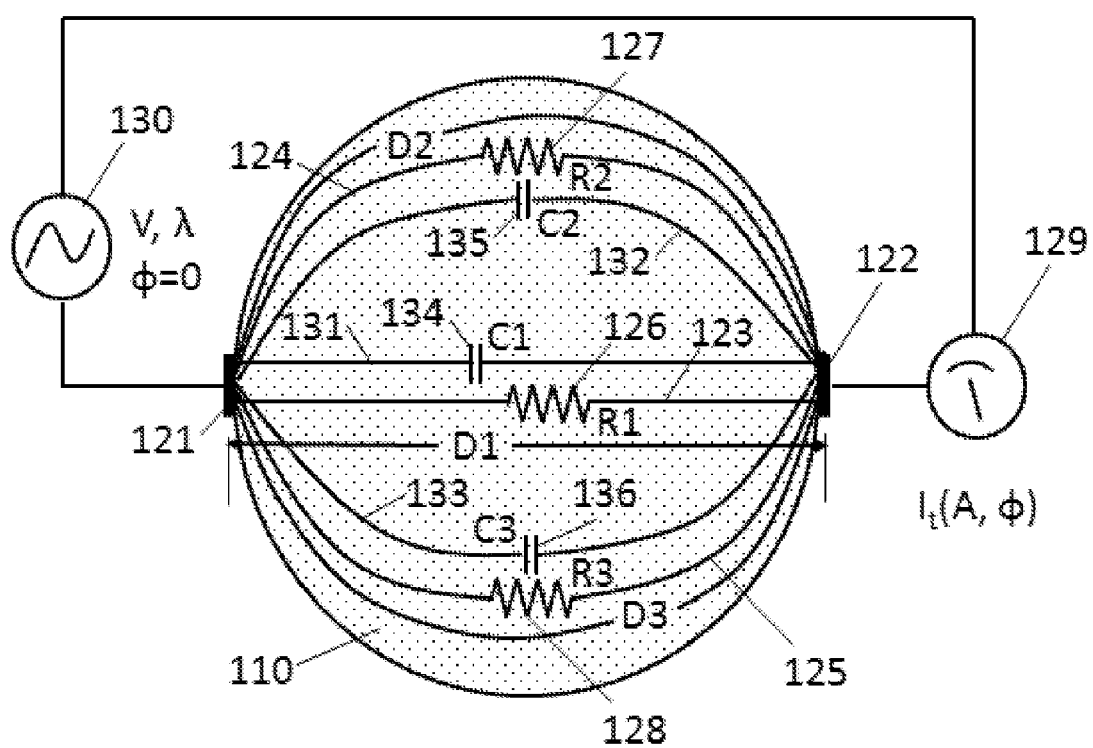
FIG. 2 illustrates the modeling of impedance properties of an object for computational purposes taking into account capacitance.

The foregoing system and method can be extended to account for capacitance effects by including capacitance branches, as shown with respect to the three-branch example in FIG. 2. Capacitances of the three branches are represented by three additional parallel paths 131, 132, 133 having capacitances, respectively, of $C_1$ 134, $C_2$ 135, and $C_3$ 136, and having lengths $D_1$, $D_2$, and $D_3$, respectively, identical to those of the corresponding resistance paths. In effect, each of the three paths is treated as a parallel RC path, and represented as two separate paths, one a pure resistance path, and one a pure capacitance path. The current due to a sinusoidal voltage signal through a capacitance is inversely proportional to the capacitive reactance, $$\frac{1}{2\pi fC} = \frac{\lambda}{2\pi cC},$$

where f is the frequency of the signal, C is the capacitance, $\lambda$ is the wavelength of the signal, and c is the speed of light in the medium through which the signal is passing. Accordingly, the expected path current I at the downstream electrode for a path with capacitance C, path length D, at interrogation wavelength $\lambda$ is given by $$I(\lambda, D, C) = V \cdot jC \cdot \left(\frac{2\pi c}{\lambda}\right)\left(\cos\left(2\pi\frac{(D - \lambda)}{\lambda}\right) + j \cdot \sin\left(2\pi\frac{(D - \lambda)}{\lambda}\right)\right)$$

The coefficient, $$\left(\frac{2\pi c}{\lambda}\right)\left(\cos\left(2\pi\frac{(D - \lambda)}{\lambda}\right) + j \cdot \sin\left(2\pi\frac{(D - \lambda)}{\lambda}\right)\right),$$

depends only on D and $\lambda$ (making the assumption that c is known or can be estimated or measured and that the medium is isotropic regarding c along the path in question). Therefore, the linear system describing the currents measured at the downstream electrode 122 (see FIG. 2) is given by:

$$\left(\frac{I_n}{V_n}\right) = \left\{\left(\cos\left(2\pi\frac{(D_m - \lambda_n)}{\lambda_n}\right) + j \cdot \sin\left(2\pi\frac{(D_m - \lambda_n)}{\lambda_n}\right)\right),\right.$$
$$\left.\left(\frac{2\pi c}{\lambda_n}\right)\left(\cos\left(2\pi\frac{(D_m - \lambda_n)}{\lambda_n}\right) + j \cdot \sin\left(2\pi\frac{(D_m - \lambda_n)}{\lambda_n}\right)\right)\right\}\left\{\frac{1}{R_m},\atop jC_m\right\}$$

Where $$\left(\frac{I_n}{V_n}\right)$$

is again a vector of measured currents upon applying sinusoidal voltage signals of amplitude $V_1 \ldots V_n$ and wavelengths $\lambda_1 \ldots \lambda_n$ between electrodes 121 and 122 (such currents expressed in complex form); the matrix of coefficients $$\left\{\left(\cos\left(2\pi\frac{(D_m - \lambda_n)}{\lambda_n}\right) + j \cdot \sin\left(2\pi\frac{(D_m - \lambda_n)}{\lambda_n}\right)\right),\right.$$
$$\left.\left(\frac{2\pi c}{\lambda_n}\right)\left(\cos\left(2\pi\frac{(D_m - \lambda_n)}{\lambda_n}\right) + j \cdot \sin\left(2\pi\frac{(D_m - \lambda_n)}{\lambda_n}\right)\right)\right\}$$

is a n (rows) by 2 m (columns) matrix of coefficients, in alternating columns as shown, with the odd numbered columns corresponding to resistance paths and determined according to the expression $$\left(\cos\left(2\pi\frac{(D_m-\lambda_n)}{\lambda_n}\right) + j\cdot\sin\left(2\pi\frac{(D_m-\lambda_n)}{\lambda_n}\right)\right),$$

and the even numbered columns corresponding to capacitance paths and determined according to the expression $$\left(\frac{2\pi c}{\lambda_n}\right)\left(\cos\left(2\pi\frac{(D_m-\lambda_n)}{\lambda_n}\right) + j\cdot\sin\left(2\pi\frac{(D_m-\lambda_n)}{\lambda_n}\right)\right); \text{ and}$$

$$\left\{\begin{array}{c}\frac{1}{R_m},\\ jC_m\end{array}\right\}$$

is a vector of unknown values of $1/R_m$ and $jC_m$ to be solved for, with the odd numbered rows representing $1/R_m$ values and the even numbered rows representing $jC_m$ values. The $C_m$ values (or, alternatively, the matrix coefficients for the even numbered columns) are multiplied by j so as to account for the 90 degree phase shift caused by the capacitance. A Mathematica program implementing the foregoing methods and illustrating the 3-resistance path, 3-capacitance path example using specific numeric values follows as Appendix A. The values shown therein are not intended to be physiologically realistic, but merely to illustrate the application of the method and show how it may be implemented in software.

Inductance is usually thought to be negligible in physiological media, and has not been accounted for in the foregoing example. It will be apparent, however, that the model is easily extended to account for inductance by including additional paths for the inductances in the same manner as has been done for the capacitances, and including appropriate coefficients taking into account inductive reactance and the 90 degree phase shift caused by inductance in the opposite direction from the phase shift caused by capacitance. Doing so would obviously necessitate interrogating at a number of additional frequencies at least equal to the number of inductance paths added. It will also be apparent that the model is readily extended to series capacitances and/or inductances where the characteristics of a particular system or medium are better captured by such an extension.

The model described above and illustrated in the example can be generalized to any arbitrary number of paths, limited only by the number of interrogation frequencies applied, the computational resources available to handle the large matrices that result from large numbers of paths, and the ability to measure currents with sufficient accuracy.

Application of System and Method as to Continuous Medium

Figure 3:
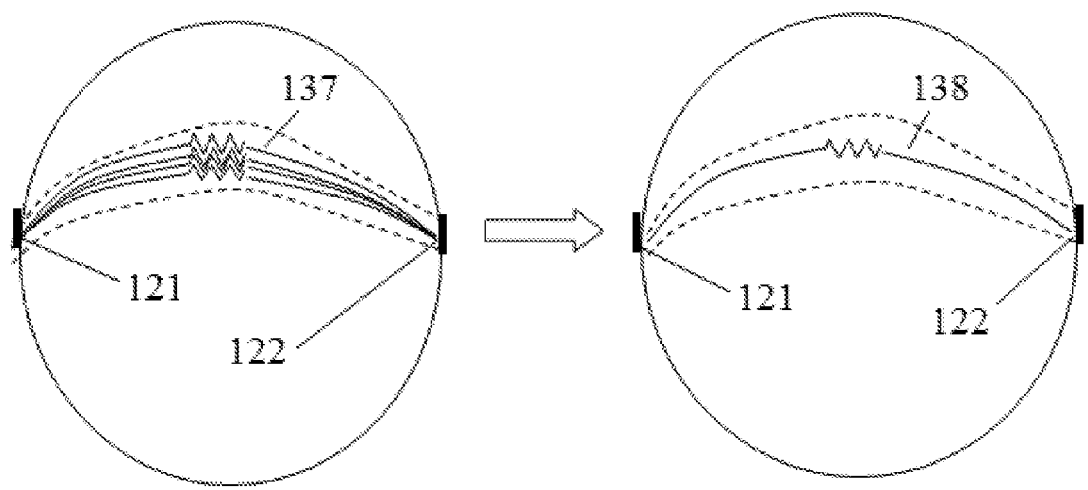
FIG. 3 illustrates the modeling of impedance properties of a region by a single lumped impedance.

Obviously, the foregoing example, dealing as it does with a finite number of discrete paths, differs from the type of measurement desired for imaging purposes, where the conductive properties of the object being measured are continuous. To understand how the systems and methods disclosed herein may be used for estimating the impedance of a continuous two or three dimensional object along a straight line path between two electrodes, it will be convenient to consider the configuration shown in FIG. 3. Any predetermined group of paths 137 (referred to herein as 'component paths') may in principle be represented in the model by a single path 138 (referred to herein as a 'lumped path'). If this is done, the lumped path values determined by the model will be expected to underestimate the aggregate of the composite path currents, and therefore overestimate the impedance. This is so because the component paths are of unequal lengths. Therefore the currents on such component paths are delayed relative to the interrogation signal by varying time intervals in their arrival at the downstream electrode 122, so they are out of phase with each other to varying degrees. The 'true' aggregate current representing the true impedances of the component paths is the in-phase sum of all the component path currents represented by the 'lumped' path; to the extent that any of the component path currents is out of phase with the others, the aggregate current must be reduced from the 'true' aggregate current when the component path currents are superposed.

The extent to which the 'lumped' shunt path current underestimates the 'true' aggregate of the currents on the paths represented by the 'lumped' shunt path depends upon the distribution of the path lengths of such paths. In general, the narrower the distribution of path lengths of the component paths 137, so that the variation in path length among the component paths is relatively small, then the smaller will be the difference between the 'true' aggregate current and the lumped path current obtained by the model. If the distribution of the component paths is known or can be estimated, then it is possible to compute a correction factor for the average expected error based on the attenuation to be expected given the distribution of paths present, the interrogation frequency, and an assumed distribution of current amplitudes among the component paths.

For imaging purposes, therefore, a somewhat crude measure of the straight line path impedance can be obtained using the analysis described herein with only two paths: the straight line path for which the path length $D_1$ is measured directly as the distance between electrodes; and a single shunt path, whose path length $D_2$ is determined arbitrarily as a reasonable 'lumped' shunt path based on the known geometry of the object being imaged. For example, for an object that is approximately symmetrical about the straight line path, any path coplanar with the straight line path and equidistant between the straight line path and the boundary of the object might reasonably be taken as the lumped shunt path. A minimum of four interrogation signals at different frequencies is applied to the electrodes in the manner already described, and, for each frequency, the current amplitude and phase is measured at the downstream electrode and, for convenience, converted to a complex value. The linear system described herein is solved and the straight line path resistance and capacitance are computed. The procedure is repeated for a plurality of other electrode pair locations. From the resistance (and optionally capacitance) values obtained for the various straight line paths, an image may be constructed by any of the well known methods for constructing an image from line integrals, such as back projection or Fourier analysis.

An Embodiment

Because the expected underestimation of currents depends upon the range of path lengths represented by the lumped paths, it is desirable to reduce the range of path lengths of the component paths corresponding to each lumped path as much as possible. Therefore, a preferred embodiment of the system and method of the invention proceeds, in general, as follows: First, a plurality of electrode pair placements is determined, in such a way that the straight line paths between the chosen electrode pair positions are spatially distributed in a manner suitable for image reconstruction by back projection when the impedances of such straight line paths have been determined, at the desired resolution.

Then, for each electrode position pair so determined, the impedance properties of the paths between the two electrodes are determined using the methods described herein, and in general as described in this paragraph. First, unless it is known a priori, the distance $D_1$ between the two electrodes is measured using a caliper. (As used herein, "caliper" shall mean any apparatus now known or existing at any future time, and any equivalent thereof, whose function is to measure the straight line distance between two points in space.) A distance $D_{MAX}$, being the longest current path to be analyzed, is also determined by measuring or estimating the longest distance between the two electrodes along the circumference of the object being imaged, and coplanar with the straight line path. (It is recognized that, in theory, current can take convoluted paths that could be much longer than a direct circumferential path, but it is believed that as a practical matter the currents attributable to extremely long paths may reasonably be neglected for imaging purposes. The determination of $D_{MAX}$ can be made in many possible ways; the method described is merely one preferred method.) It is then necessary to determine the number of shunt paths to be analyzed, which also determines the number of interrogation frequencies to be applied. In this preferred embodiment, approximately 100 shunt paths is considered a suitable number; taking into account capacitance paths, this results in a linear system of rank approximately 200, which is readily and quickly solvable on a typical personal computer using appropriate software. The lengths of the assumed shunt paths are distributed evenly over the range from $D_1$ and $D_{MAX}$, inclusive. Interrogation frequencies are then selected. The number of frequencies must at least equal the number of path lengths; it is recommended that a larger number be used, in case any readings must be discarded on account of error or in case it is desired to select those frequencies that best optimize the conditioning of the coefficient matrix. Selection of the frequency range depends upon several competing considerations. Interrogation signals of shorter wavelengths are desirable from the standpoint of giving larger relative phase shifts between paths, making the system less sensitive to measurement error. However, very short wavelengths (i.e. in the microwave range) do not propagate well in tissue, cause local heating effects, and may cause artifacts if the difference between the lengths of any two paths is greater than half the wavelength, since in that case the two currents shift in phase with respect to each other enough to return to more or less in-phase alignment. It is believed that for purposes of physiological imaging, interrogation signal wavelengths ranging from on the order of a minimum ($\lambda_{MIN}$) approximately three or four times $D_{MAX}$ to a maximum ($\lambda_{MAX}$) of approximately 20 times $D_{MAX}$ represent an appropriate compromise for this preferred embodiment. The invention is not, however, limited to such frequencies, and, as is apparent from the discussion above, in principle any frequencies can be used. The desired number of interrogation wavelengths may be distributed evenly over the range from $\lambda_{MIN}$ to $\lambda_{MAX}$; it may also be deemed desirable to then adjust each of these evenly distributed wavelengths by a small random factor so as to avoid wavelengths that are even multiples of other wavelengths. This adjustment is believed to possibly improve the conditioning of the coefficient matrix. A steady state sinusoidal signal of constant voltage amplitude at each interrogation frequency is applied in turn at one of the electrodes, and the amplitude and phase of the current is measured at the other electrode, in the general manner shown in FIG. 2 and described above. These current amplitudes and phases are converted to complex values, those values are divided by the voltage amplitude of the applied signal, and the resulting complex values are assembled into the vector of observed currents $$\left(\frac{I_n}{V_n}\right).$$

(In this preferred embodiment, the same voltage amplitude is used for all interrogation signals; however, it is possible to use a different voltage for each.) From the distribution of path lengths and the distribution of interrogation signal wavelengths, the coefficient matrix is assembled as described above. The linear system is then solved for the resistances and capacitances of each of the approximately 200 paths (100 resistance paths and 100 capacitance paths). The straight line path resistance and capacitance are noted for the electrode pair position in question. (In this preferred embodiment, the other values are not used.)

Having thus determined values for the resistance and capacitance of the straight line path for all of the selected electrode position pairs, an image is then constructed by back projection or by Fourier analysis.

Another Embodiment (Finite Element Approach)

In another preferred embodiment, a finite element representation of the object to be imaged is first determined, having a predetermined number of nodes at selected positions on the exterior of the object, an additional predetermined number of nodes at selected positions in the interior of the object, and edges joining neighboring nodes. The determination of the number and positions of nodes and the choice of node pairs to be connected by edges is accomplished in accordance with methods that are well known to persons having ordinary skill in the art of finite element analysis of the electrical properties of two and three dimensional objects. Pairs of exterior nodes, preferably on generally opposite sides of the object, are selected for application of the interrogation signals, thus establishing a set of electrode position pairs. The number of pairs to be included in the set is at least sufficient to determine a linear system as described below.

For each electrode position pair, a set of path impedances is determined as follows: First, the desired number of interrogation frequencies is determined. This should be at least equal to twice the number of edges in the finite element grid, and optimally a larger number should be used in case any readings must be discarded on account of error, in case it is desired to select those frequencies that best optimize the conditioning of the coefficient matrix, or in case the geometry of the finite element grid turns out to be such that some edges are not adequately interrogated by fewer frequencies. Then the number of paths to be analyzed is determined; this should be at least twice the number of edges in the finite element grid. Next, the possible paths through the grid between the two electrode nodes are enumerated in order by path length. For smaller grids, this may be done by enumerating all possible paths and sorting them by length; for larger grids, the number of possible paths makes this impracticable, and Monte Carlo methods may be used, or methods may be applied to generate the possible paths in ascending order by length, where the grid topology lends itself to such methods. The result of this analysis will be a list of at least as many paths, ordered by path length, as required to produce a number of path lengths equal to the number of paths to be analyzed as previously determined. A pair of electrodes is then placed on the object at the predetermined positions, the interrogation signals are applied, and the amplitudes and phases of the resulting currents are recorded as before. A coefficient matrix is constructed as before from the predetermined path lengths and interrogation signal wavelengths, and the linear system is solved for the resistance and capacitance of each of the predetermined path lengths.

When the analysis described in the preceding paragraph has been completed for each of the predetermined electrode position pairs, another linear system is constructed in which each row represents the equation for one path, as follows:

$$R_{PATH} = \sum_K R_{EDGE},$$

where $R_{PATH}$ is the total resistance of the path, $R_{EDGE}$ is the resistance of a single one of the edges comprising the path, and K is the number of edges comprising the path. This linear system can then be solved for the resistances of the edges. Using the path capacitances determined for all the paths, the capacitances of the edges can be similarly determined, keeping in mind that serial capacitances combine as $$\frac{1}{C_{PATH}} = \sum_K \frac{1}{C_{EDGE}}.$$

It may be necessary to adjust the number of paths included in the system, and to determine which paths should be used assuming data has been taken for a sufficient number of paths to overdetermine the system, in such a way as to optimize the conditioning of the system and allow determination of values for all edges. Since this approach results in resistance and/or capacitance values for all edges in the finite element grid, it in effect directly produces what amounts to an image of the resistance or capacitance properties of the object.

2. Interrogation of Straight Line Path Using Resonant Frequency Signal

A further enhancement of the system and method described herein for estimating the magnitude of the current following a straight line path between two electrodes in its passage through a medium having multiple possible current paths involves the application of an interrogation signal of such a frequency that resonance is induced along the straight line path. It is well known that when an electrical signal is applied to a conductor at a frequency such that the length of the conductor is equal to or closely approximates one-half the wavelength of the signal in the medium of which the conductor is composed, or an integral multiple thereof, the conductor will resonate, radiating electromagnetic energy, and thereby causing its observed impedance to increase markedly at the resonant frequency as compared to its impedance at other frequencies. The quantity of energy radiated as electromagnetic energy depends, among other things, upon the amplitude of the signal applied to the conductor, which in turn is attenuated to the extent it encounters impedance in its passage through the conductor.

Figure 4:
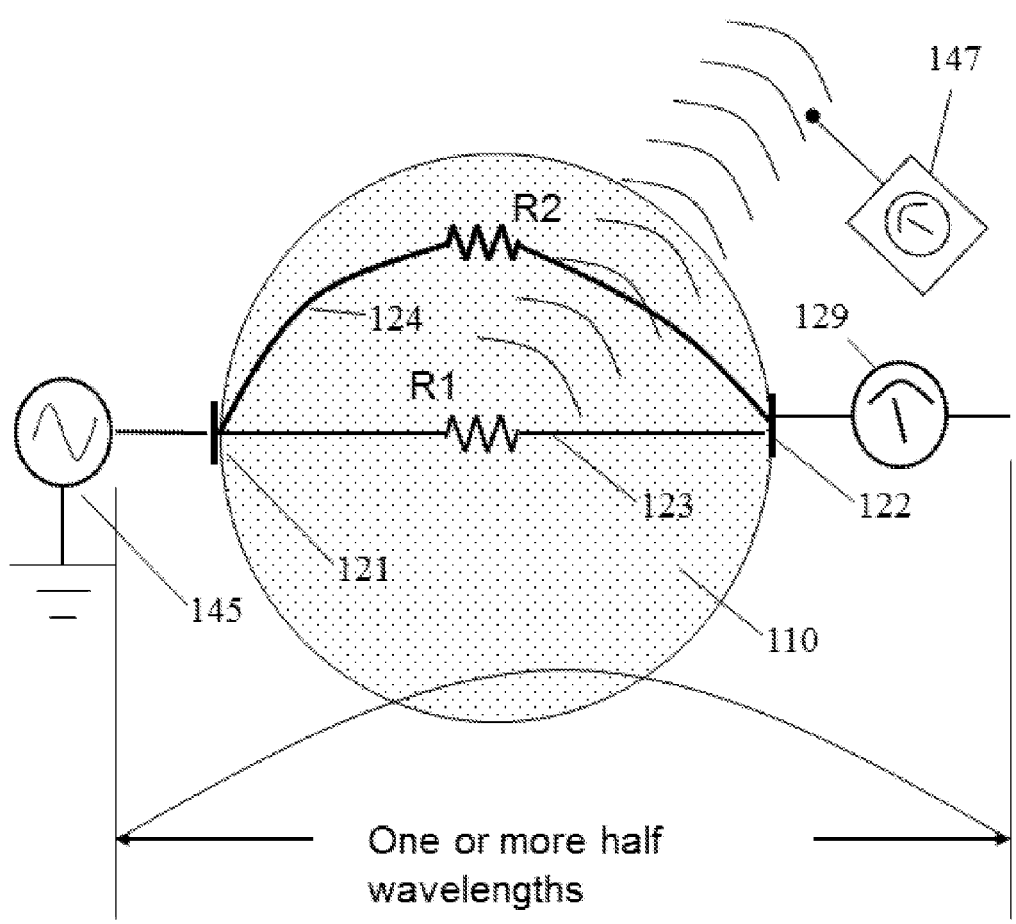
FIG. 4 illustrates feature of an embodiment of a method and apparatus for measuring impedance related properties of a conductive path.

Consider again the model previously described, in which the impedance properties of an object are represented as a resistance on a straight line path and one or more shunt resistances and/or capacitances on a longer path. As shown in FIG. 4, a signal generator 145 is used to apply a signal whose frequency is such that the half-wavelength of the signal is equal to the sum of the path length along the straight line path and the length of the conductor through which the signal is applied. The current will now be split between the straight line path 123 and the shunt path 124 in proportion to the respective impedances. However, the apparent impedance along the straight line path 123 will be greatly increased in comparison to the impedance that would be presented to a signal at a non-resonant frequency, because of the energy lost by electromagnetic radiation, while the apparent impedance along the shunt path 124 will not be increased. The magnitude of the radiation emitted from the resonant signal along the straight line path will depend in part upon the resistance and impedance properties of the medium of which the straight line path 123 is composed, since a more resistive medium will attenuate the amplitude of the signal as it passes down the conductor to a higher degree than a less resistive medium would. Therefore, the effect of the impedance properties of the conductive medium along the straight line path 123 will be relatively magnified in terms of their effect upon the observed impedance at resonance. It will be possible to improve the resolution of the determination of impedances using the system and method of the invention, by selecting interrogation frequencies each of which corresponds to a half-wavelength of which the straight line path or one of the predetermined shunt paths is an integral multiple, so that each path used in the analysis is interrogated by a signal that is resonant along such path.

It will also be possible to use this resonance effect directly to provide an imageable measure related to the impedance along the straight line path by measuring the amplitude of the electromagnetic field radiated at resonance. The amplitude of the electromagnetic field radiated from the resonating signal along the straight line path will be inversely related to the impedance properties of the medium comprising the path. In a preferred embodiment taking advantage of this effect, a plurality of electrode pair placements is first determined, in such a way that the plurality of straight line paths between the chosen electrode pair positions are spatially distributed in a manner suitable for image reconstruction by back projection when the impedances of such straight line paths have been determined. Then, for each electrode position pair so determined, electrodes 121, 122 are placed as illustrated in FIG. 4 and a signal generator 130 is used to apply an interrogation signal of predetermined amplitude and having a half-wavelength chosen so as to induce resonance in the straight line path 123 between electrodes through the object being measured. (This may be accomplished by applying a signal of whose half-wavelength the straight line path is an integral multiple, or, using a longer wavelength signal, by inducing resonance in the straight line path together with a conductor of predetermined length by which the signal is applied, as illustrated in FIG. 4. It will be possible to determine the correct frequency by beginning at a wavelength that is longer than that required to induce resonance along the straight line path; such a wavelength will instead induce resonance along some longer path through the object. The frequency will then be gradually increased while observing the intensity of the radiated signal. Since the straight line path is the shortest possible path, when the frequency is raised to a point such that the wavelength is slightly less than that required to induce resonance in the straight line path, no path will resonate, and the intensity of the radiated signal will abruptly decrease. In this way, the frequency required to induce resonance in the straight line path can be determined.) The intensity of the electromagnetic radiation so induced will then be measured using a field strength measuring instrument 147, which may include and/or operate according to any of the many methods known to persons having ordinary skill in the art for detecting and quantifying electromagnetic radiation. When such measurements have been made for each of the predetermined electrode position pairs, the set of measured intensities, each of which represents a measure of the impedance of the straight line path between the electrode pair to which it corresponds, may be used to generate an image of the impedance properties of the object by any of the well known methods for generating images from line integrals of physical properties of an object, such as back projection or Fourier analysis.

Thus, provided herein is a method of estimating a measure of an impedance property between a first locus and a second locus separated by a conductive medium having at least two electrically conductive paths between the first locus and second locus, wherein the method includes introducing at the first locus an alternating electrical signal at a frequency at which at least one conductive path resonates, and measuring the intensity of electromagnetic radiation emitted by the at least one conductive path that resonates. In embodiments, a conductor may be connected to the second locus, and the at least one conductive path that resonates may include all or part of the conductor. In embodiments, the length of the conductive path from the first locus to the end of the conductor connected to the second locus should preferably be an integral multiple of a half-wavelength of the alternating electrical signal so as to produce maximum resonance. However, it will be apparent that the important consideration is the length of the overall resonating path, and that any configuration including a shortest length conductive path through the conductive medium combined with one or more conductors and or other components to produce a path capable of residence at the frequency of an applied alternating electrical signal may be employed. In embodiments, any of the methods known to persons of skill in the art for lowering the frequency at which an antenna resonates may be employed to reduce the length of attached conductor required and/or reduce the frequency of the alternating electrical signal. By way of example, so that resonance may be produced at a lower frequency and/or using a shorter conductor connected to the second locus, a loading coil, such as, for example, an inductor placed in series with the conductor, may be employed.

3. Method and Apparatus for Generating Images

Figure 5:
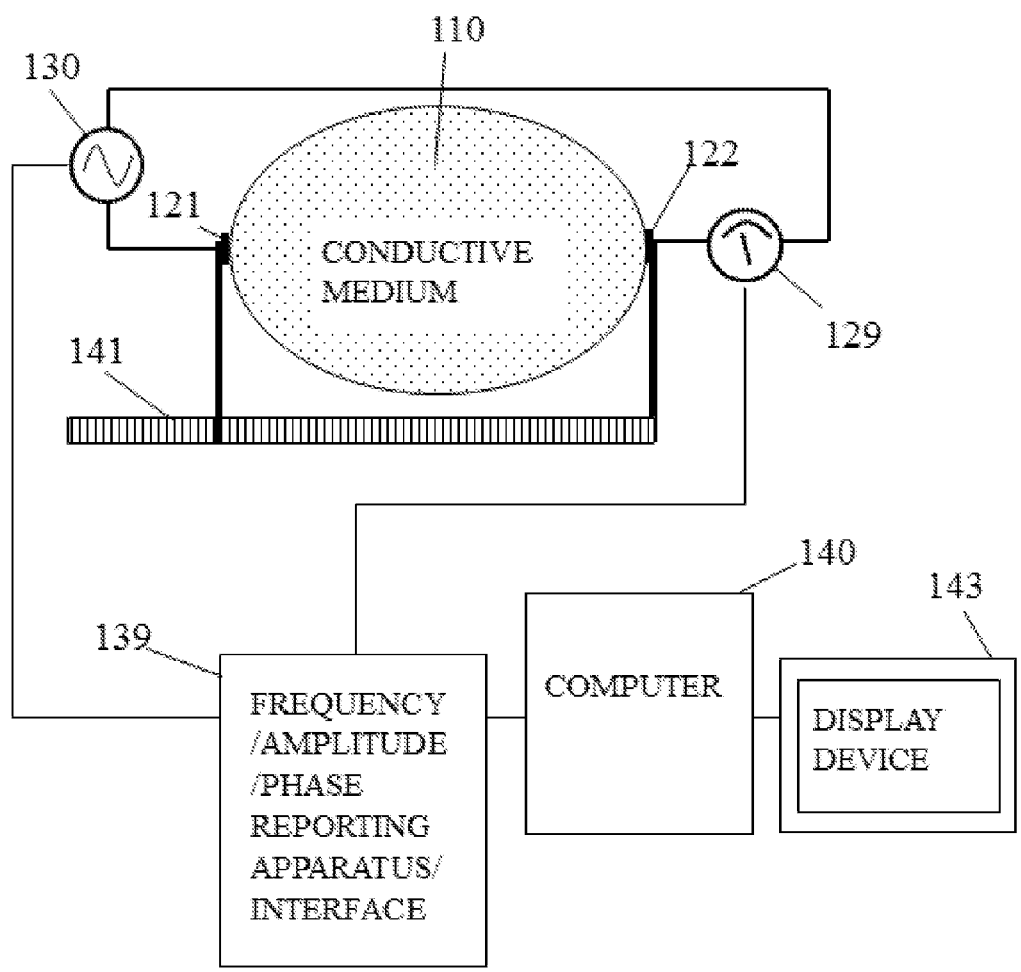
FIG. 5 illustrates an embodiment of an apparatus for measuring impedance related properties of an object.

Based on the system and methods described herein, an apparatus can be constructed for producing images. In a preferred embodiment, as shown schematically in FIG. 5, such an apparatus would comprise a signal generator 130 capable of generating interrogation signals at the desired amplitudes and frequencies; a set of electrodes 121 122 and leads; a caliper 141 for measuring the straight line distance between electrodes; an instrument 129 for measuring accurately the amplitude of the current at the downstream electrode and its phase relationship with the interrogation signal; an apparatus 139 for reporting the frequency, amplitude and phase of the interrogation signal and the amplitude and phase of the measured current signal and interfacing with a computer so as to report such data in a form useable by the computer; and a programmable computer 140 programmed to carry out the analysis described herein, to generate an image from the data so provided, and optionally to display such image on a suitable display device 143 such as a monitor or printer.

The computations to be performed in connection with this invention may, of course, be incorporated in software and implemented on the hardware of a computer programmed in accordance with the methods described herein. The invention is intended to extend to the apparatus comprising a computer programmed to carry out the method of the invention, and to machine readable media upon which has been written or recorded a computer program for carrying out the method of this invention. The methods and apparatus of the invention may also be incorporated as part of an imaging apparatus for producing images representing the impedance properties of a sample by analyzing measurements taken between a plurality of electrode pairs using existing methods of producing an image from line integral measurements. Such methods are well known in the field of computed tomography. The invention is intended to extend to any such imaging apparatus incorporating the methods of the invention.

4. Estimating Path Impedance From Response to an Applied Potential

Figure 6A:
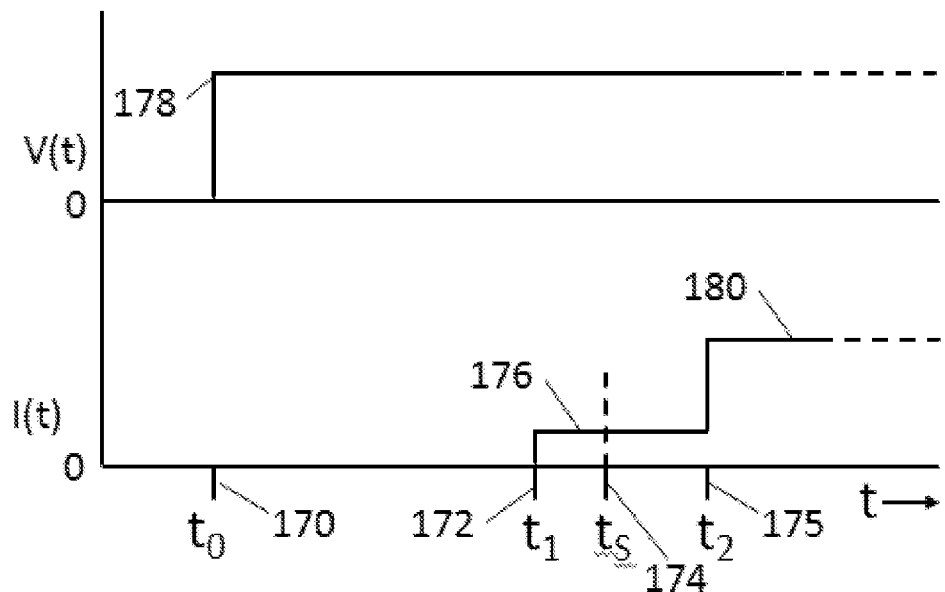
FIGS. 6A and 6B depict aspects of an exemplary signal as would be observed in an embodiment of a method or apparatus for estimating an impedance property of a path of interest in a conductive medium.

In a conductive medium 110 as represented in the simplified model of FIG. 1, when a potential is applied across the electrodes 121, 122, the resulting current will require a longer time to propagate via the longer shunt paths 124, 125 than via the shortest path 123. Therefore if a step potential V 178 is applied at time $t_0$ 170 as illustrated in FIG. 6A, the current measured at the downstream electrode 122 will remain zero during the transit time required for the signal to propagate from the upstream electrode, which for the shortest path 123 is the distance D1 (that is, the length of the shortest distance path between the electrodes), divided by the speed of electromagnetic propagation c in the conductive medium. As illustrated in FIG. 6A, at time $t_1$ 172 equal to $t_0$ plus the shortest path transit time, the signal passing along the shortest path will begin to arrive at the downstream electrode and the corresponding current 176 will be observed. After additional time passes, the signal passing along the longer shunt paths 124 125 will begin to arrive at the downstream electrode, with the corresponding shunt path current superposing with the shortest-path current at the electrode 122. Thus as illustrated in FIG. 6A, for the simplified representation of FIG. 1, the signal passing along the two shunt paths D2 and D3 (here assumed of equal length) arrives at the electrode 122 at time $t_2$ 175 equal to $t_0$ plus a transit time equal to the path distance (D2 or D3) divided by the speed of electromagnetic propagation c in the conductive medium. Since D2>D1, it follows that $t_2 > t_1$. Considered from the standpoint of the apparent resistance, the current I(t) at electrode 122 may be thought of as passing initially only through the shortest path resistance R1; after sufficient time has passed for the signal to propagate through the longer shunt paths, the current is determined by V divided by the lower combined resistance of all three parallel resistance paths. Thus as illustrated in FIG. 6A, between time t1 and t2, the observed current 176 is equal to $$V\left(\frac{1}{R1}\right),$$

and after time t2, the observed current 180 is equal to $$V\left(\frac{1}{R1} + \frac{1}{R2} + \frac{1}{R3}\right).$$

The current can be measured at a time $t_S$ 174 during the interval after $t_1$ but before $t_2$, providing a measure of the resistance R1 of the shortest path. Thus for this system a measure of the shortest path impedance can be estimated by observing the current I at the downstream electrode 122 at a time $t_S$ within a time window commencing at time $t_1$ and ending at time $t_2$, and dividing the applied step potential V by the observed current I.

The foregoing method can be generalized to conductive systems having more than two conductive paths, and/or including continuous media. In conductive systems involving continuous media, there may be many geometrically possible paths that carry little or no current, such as, for example, paths that are circuitous or retracing or that would entail current flows against a potential gradient. In analyzing such systems it may be found useful to ignore these paths and limit the analysis to current-contributive paths; that is, conductive paths that carry a current that is not zero and not of insufficient magnitude to be of significance in a computation of interest (such as, for example, an estimate of shortest path impedance, an estimate of the spatial distribution of impedances, or computation of an image) when a potential is applied at one end of the path relative to the other and a steady state has been reached. Thus although in theory there could be current flows on paths of arbitrary lengths and geometries, in general the current contribution of most very long paths, circuitous paths, paths having multiple inflection points or retracements, and the like will be insignificant and can be neglected. In conductive media or objects of practical interest, there may typically be defined or estimated a longest current-contributive path length, that is, the length of a longest path reasonably expected to carry significant current. In a system having reasonably regular geometry, for example, a longest significant path length might be estimated as the longest reasonably smooth and non-retracing parabolic or elliptical path passing adjacent to a perimeter.

In some embodiments it may be found useful to represent an impedance property in terms of a composite path, which may be a composite of any set including at least one and less than all current-contributive paths. For example, it will be apparent that conductive paths in a continuous medium need not necessarily be represented as one-dimensional or as of infinitesimal lateral extent, but rather, in an embodiment, may also be two- or three-dimensional and/or of any shape or extent found useful for an application of interest. In some embodiments and/or in conductive systems involving continuous media and/or a larger number of conductive paths, it may be found useful to represent impedance properties of the conductive medium in terms of lumped paths, as disclosed in a preceding section. In some embodiments, it may be found useful to represent impedance properties in terms of paths representing a portion of the volume of the object or medium, such as, for example, a generally cylindrical path or a path comprising the walls of a cylinder or tube. In some embodiments, it may be found useful to represent impedance properties in terms of a path corresponding to an aggregate or subset of all possible current-contributive paths, such as, for example, a path representing all current-contributive paths between a first point and a second point having a length less than an arbitrary length L, or a path representing all current-contributive paths between a first point and a second point having a length less than an arbitrary length L1 and greater than an arbitrary length L2.

Figure 6B:
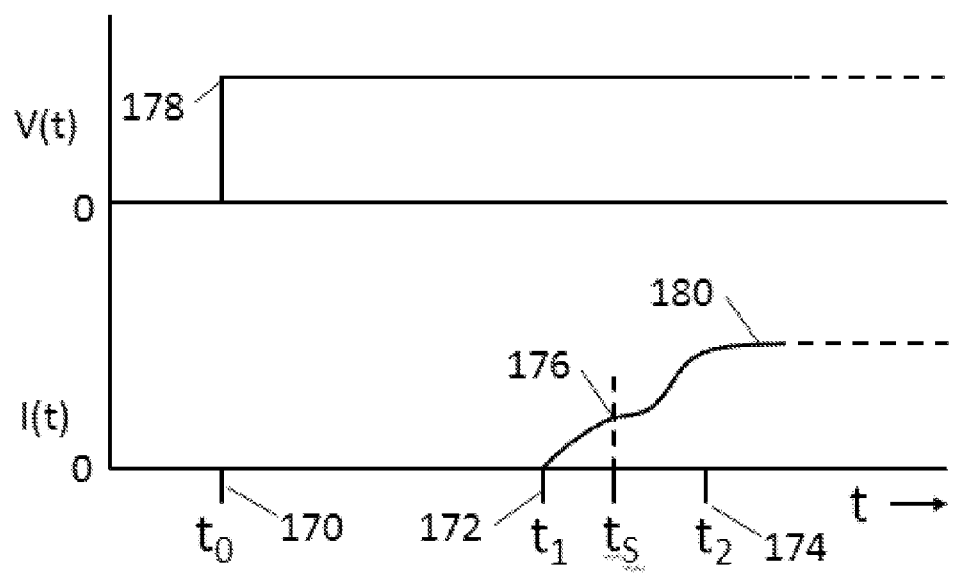

As illustrated in FIG. 6B, for a conductive system having a relatively larger number of current-contributive conductive paths, as with the simplified representation already described, no current will be observed at a second point in response to a potential applied at a first point until the shortest path transit time has elapsed, after which the observed current at the downstream electrode will rise as the currents propagating along increasingly longer conductive paths arrive. For a step potential V 178 applied at a first point at time $t_0$ 170, and considering first a system having an arbitrary number of current-contributive conductive paths in which the impedances are entirely resistive, a downstream current will again begin to be observed at a time $t_1$ equal to $t_0$ plus the shortest-path transit time, and rise to a steady state value 180 at a time $t_2$ when sufficient time has elapsed for the signal to propagate along all the current-contributive paths. At a sampling time $t_S$ after $t_1$ and before $t_2$, the observed current at the downstream electrode will be a superposition of the currents propagating along some but not all the available current-contributive paths. If the downstream current is sampled at a time $t_S$ close to $t_1$, the observed current will be a superposition of, and a measure of the impedance of, the shorter paths. As the sampling time $t_S$ is delayed further from $t_1$, the superposition will include currents propagating along additional increasingly longer conductive paths, until eventually all the current-contributive paths are included and a steady state current is reached at time $t_2$. Thus the observed downstream current can be taken as a measure of the impedance of a lumped path consisting of all the current-contributive conductive paths that are shorter than $(t_S-t_1)$ c, where c is the speed of electromagnetic propagation in the medium. Accordingly, the theoretically most accurate representation of the impedance of a straight line path will be obtained by keeping $t_S-t_1$ to a minimum to the extent feasible, taking into account the capabilities of the measuring instrumentation used and the need to minimize measurement error. Thus in some embodiments wherein measurements are to be used for imaging or for estimating a spatial distribution of impedance, a tradeoff may be found to exist between measurement accuracy, which may be compromised if the sampling time $t_S$ is very soon after t1 since the current will then be relatively small, and resolution, which may be compromised to the extent that the spatial extent of lumped paths is greater, as will occur as the sampling time $t_S$ is moved closer to the steady state time $t_2$.

Figure 9:
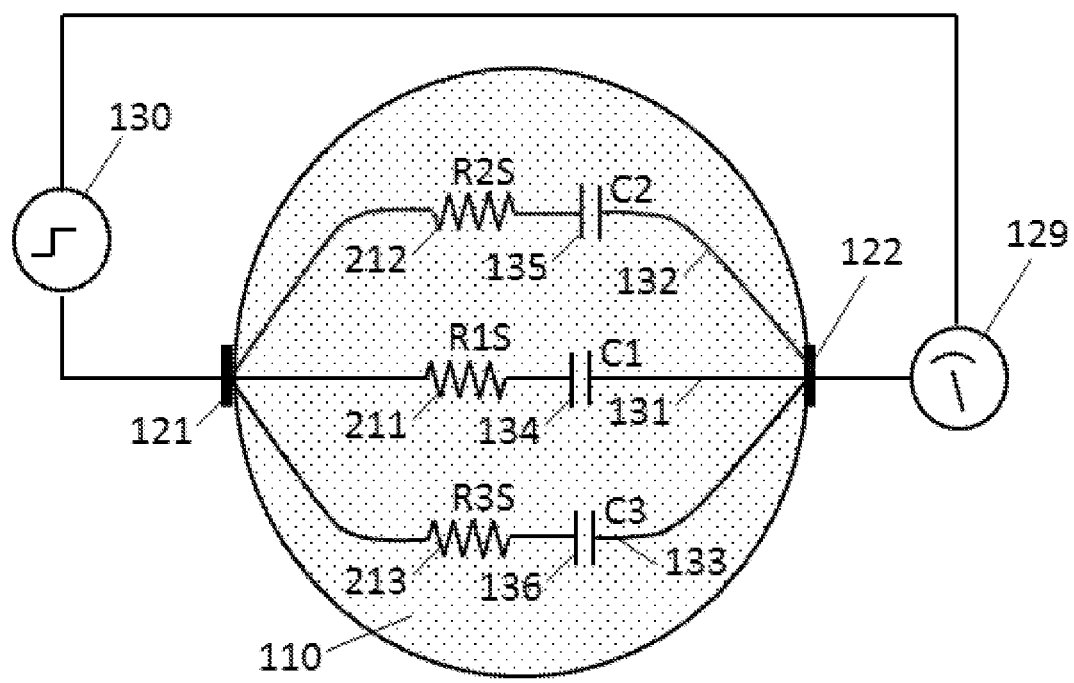
FIG. 9 illustrates the modeling of capacitive conductive paths.

In many conductive systems of practical interest for imaging, the impedance of the medium may have a capacitive component. In such a system each conductive path between electrodes may be represented as a pure resistive path in parallel with a capacitive path as illustrated in the simplified representation of FIG. 2. For clarity, the capacitive paths are shown separately in FIG. 9, with their series-resistive components represented by resistances R1S 211, R2S 212, and R3S 213. Upon applying a step potential V 178 at time $t_0$ at the upstream electrode 121 and considering only the shortest capacitive path 131 of length D1, again no current will be observed at the downstream electrode until time $t_1$ equal to $t_0$ plus the transit time D1/c. Immediately after time $t_1$, a current due to the capacitive path 131 will be observed, initially equal to the potential V divided by the series resistance R1S, and declining to zero as the capacitance becomes charged. For a step potential, once a steady state is reached there is no current flow through the capacitive path. However, the time required to reach this steady state is determined by the time constant RC (the capacitance times the series resistance), which, for the conductive media typically of interest for imaging, will typically be long compared to the transit time D1/c. Therefore a current observation taken at a time $t_S$ where the interval $t_S-t_1$ is small can be taken as an estimate of the impedance of the lumped path representing all conductive paths of length less than or equal to length $(t_S-t_0)/c$, taking into account the series resistance of the capacitive paths. To the extent the current due to capacitor charging is not negligible, such as where $RC\gg(t_S-t_0)$ does not hold, then the measure of resistance obtained by measuring the current will include a component attributable to the series resistance R1S, but will nevertheless provide a useful measure of an impedance property representing a combination of resistive and capacitive paths. If desired, measured or estimated currents and/or impedance properties can be corrected to account for the capacitive effects, such as, for example, by applying corrections based on estimates or measurements of the bulk capacitance of the medium and/or the estimated distribution of capacitance in the medium.

In an embodiment, it may be found useful to sample the current I at the downstream electrode in response to a potential V applied at the upstream electrode at time $t_0$ at any sample time $t_S$ at which the observed current I includes current propagating along at least one and less than all the available current-contributive conductive paths between the electrodes. To do this, the current should preferably be sampled at a time $t_S$ prior to the time $t_2$ at which the downstream current includes currents from all current-contributive paths.

In some embodiments it may be found useful to consider the sampling delay interval (that is, the time interval between the time at which a potential is applied at a first point in a conductive system and the time at which a sample, observation, measurement or estimate is taken at a second point in the conductive system), by reference to the minimum transit time (that is, the minimum time required for an electromagnetic signal to travel from the first point to the second point at the speed of electromagnetic propagation c in the conductive medium under the conditions of interest, along the path that results in the shortest transit time, usually the shortest conductive path). In an embodiment, the minimum transit time may be determined or estimated in any manner providing a reasonable approximation or estimate thereof, such as, for example, by computing the theoretical time required for the signal to propagate from the upstream electrode to the downstream electrode along the shortest available conductive path as described above; by observing when a non-zero current first becomes detectable at the downstream electrode following application of a potential at the upstream electrode; or by any combination of the foregoing. Similarly, it may be found useful to consider a maximum transit time, that is, the time required for an electromagnetic signal to travel from a first point in a conductive system to a second point at the speed of electromagnetic propagation c in the conductive medium under the conditions of interest, along the current-contributive path that results in the longest transit time, usually the longest current-contributive path). In embodiments, any available information regarding the geometry, composition, and/or properties of the conductive system and/or medium may be taken into account in computing or estimating transit times, impedance properties, or any other quantities useful in carrying out the methods disclosed herein, and may be obtained or estimated by direct measurement, by modeling or theoretical analysis, or in any other manner.

For a sampling delay interval longer than the minimum transit time and shorter than the maximum transit time, the length of the longest conductive path represented in a lumped path will be proportional to the sampling delay interval. (For strict proportionality it is necessary to assume homogeneous electromagnetic signal propagation properties within the conductive medium; to the extent this assumption does not hold, there may be deviation from strict proportionality, which may affect the exact composition of the set of paths represented in a lumped path, but a sample will nevertheless be a representation of some aggregation of paths and therefore a measure of a potentially imageable and/or spatially localizable impedance property of the medium.) Thus in a continuous medium the spatial extent of the lumped path may be controlled by reference to the minimum transit time. In embodiments, the sampling delay interval may be any time interval operable to provide an estimate or measure of an impedance property of a lumped path including some but not all conductive paths carrying significant current. In a preferred embodiment, the current is measured at the downstream electrode at a time $t_S$ selected such that the ratio of the sampling delay interval ($t_S-t_0$ in the examples above) to the minimum transit time ($t_1$ in the examples above) is greater than 1 and less than about 1.2. In a more preferred embodiment, the sample time $t_S$ is selected such that ratio of the sampling delay interval to the minimum transit time is greater than 1 and less than about 1.1. In a still more preferred embodiment, the sample time $t_S$ is selected such that ratio of the sampling delay interval to the minimum transit time is greater than 1 and less than about 1.05. In some embodiments, the sample time $t_S$ may be selected such that ratio of the sampling delay interval to the minimum transit time is greater than 1 and less than about 1.3, or less than about 1.5, or less than about 1.75, or strictly less than the maximum transit time. In some embodiments, a downstream current may be sampled, estimated, measured, or observed at a plurality of sample times, so as to provide estimates or measures of an impedance property of a plurality of lumped paths encompassing different ranges of path lengths and/or having differing spatial extent.

Estimates of impedance properties and measures thereof obtained according to the disclosed methods may be found useful for discovering differences between the properties of one portion of a conductive system and/or medium and another part, which may be correlated with other properties or functional characteristics of the system. In some embodiments, a plurality of such estimates and/or measures, corresponding to a plurality of paths, may be combined to produce or estimate a spatial distribution of an impedance property, and/or to produce an image. This may be accomplished in any manner providing a distribution or image useful for an application of interest, such as, for example, using any of the many techniques familiar to persons of skill in the art, such as back projection or Fourier analysis.

In the preceding discussion, examples have been given wherein a step potential is applied at a first point in a conductive system and a current measurement is made at a second point. In embodiments, the methods disclosed herein can be carried out using a potential other than a step potential, in which a different mapping of observed current to impedance may typically result. Nevertheless, the general principle remains valid for such alternative embodiments, that is, that a signal measured at a second point where the sampling delay interval is longer than the minimum transit time and shorter than the maximum transit time can be used to provide a measure of an impedance property of a conductive system and/or medium that is useful for imaging, spatial localization, determining spatial distribution of properties, or for other purposes. The methods and principles disclosed herein and apparatus utilizing them may be used to estimate a measure of an electrical impedance property of a subset of the set of all current-contributive conductive paths between a first point and second point in a conductive system and/or conductive medium, wherein the subset includes at least one and less than all current-contributive conductive paths. The electrical impedance property may be any property reasonably related to the electrical impedance of the subset of paths, such as, for example, resistance, current, capacitive or inductive reactance, signal attenuation, signal rise time to a predetermined level, and any combination of the foregoing. A measure of such a property may be any quantity related to or correlated with the property and found useful for an application of interest, and may be obtained in any manner as disclosed herein or known in the art, such as, for example, by direct measurement or observation or by estimating or calculating from other measured values. The preceding discussion has referred to potentials applied and signals detected at points in a conductive system or medium; it will be apparent that the points in question need not be points in the geometric sense, but rather refer to loci having a finite extent in two or three dimensions, as would be accessed by a physical electrode. These can be approximated as points, or modeled in any other manner found useful or more accurately approximating their actual geometry. The preceding discussion has referred to current as sampled at a point in or on the conductive system or medium; it will be apparent that current can be sampled at a point further downstream, such where an electrode in contact with the medium is connected to a wire or other conductor and current is measured in the wire or otherwise at some displacement from the electrode. In such cases the connection between the electrode and the detector can be considered, in effect, as part of the conductive system, in effect lengthening all paths. In embodiments, it may be found useful to keep the displacement of the detector to a minimum so as to minimize the contribution of capacitor charging to the observed currents.

An apparatus may be provided for carrying out the methods disclosed herein, and may include any apparatus operable to detect a current at a locus in or on a conductive system or medium at a sampling time $t_S$ whereby the detected current is a composite or superposition of currents flowing in response to a potential applied at another locus through at least one but fewer than all current-contributive conductive paths between the two loci. In an embodiment, an apparatus may include a detector for detecting current at a locus in or on a conductive system, and a controller for determining the sampling time at which the current is to be detected and controlling the detector to do so. In embodiments, the controller may determine the sampling time in whole or part by controlling or detecting the timing of the application of an electrical potential to another locus. In embodiments, the controller may determine the sampling time in whole or part by detecting the initial current rise. In embodiments, a controller may optionally control the timing and/or other aspects of the application of an electrical potential at another locus, and/or may control the operation and/or timing of any other components of the apparatus. In embodiments, an apparatus may include an electrical source for applying an electrical potential to a locus in or on a conductive system or medium. In embodiments, an apparatus may include one or more electrodes for making an electrical connection with a locus in or on a conductive system or medium, such as to connect an electrical source or detector to the locus. In embodiments, an apparatus may include a computer for computing or estimating a measure of an impedance property according to the methods disclosed herein, and may optionally include one or more interfaces and/or input or output devices for communicating data to and results from the computer. In embodiments, an apparatus may include a caliper or other component for use in measuring or estimating the length of a current path.

Figure 10:
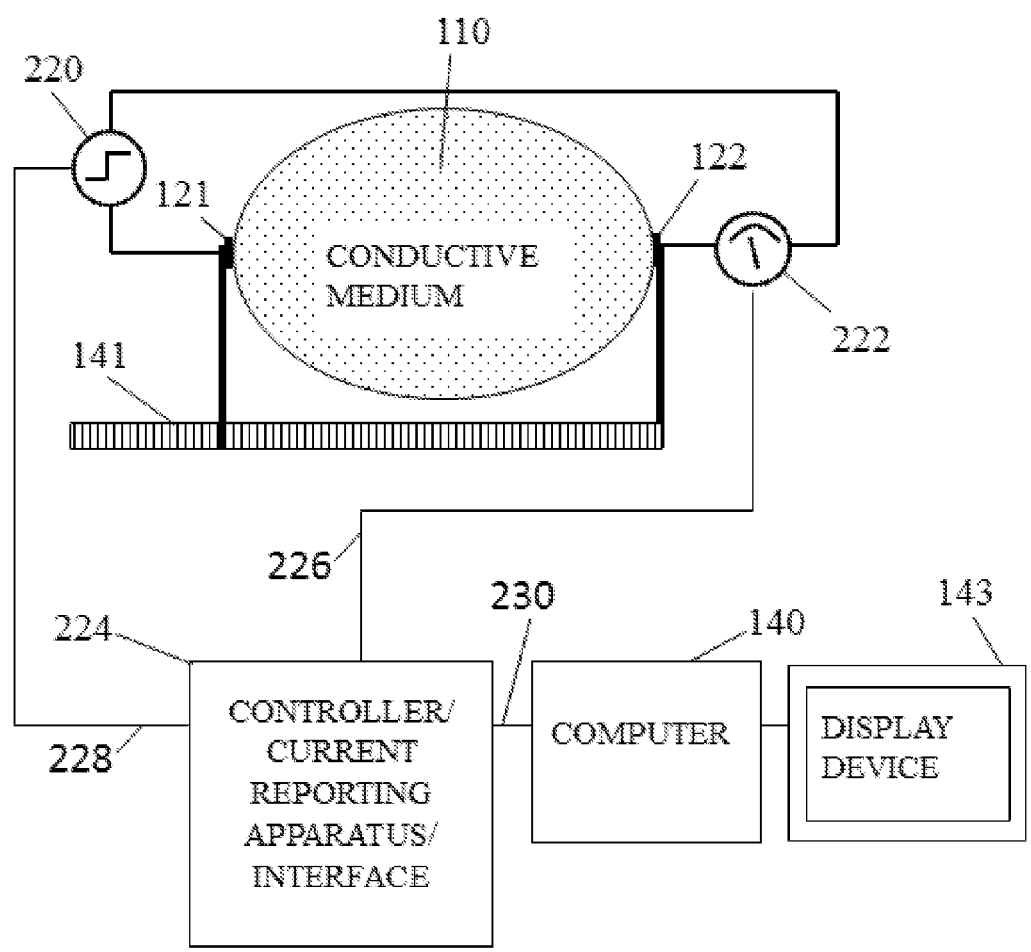
FIG. 10 illustrates an embodiment of an apparatus for measuring impedance related properties of an object.

FIG. 10 depicts an exemplary embodiment of an apparatus. An electrical source 220 is electrically connected to a point in or on a conductive system or medium 110 via an electrode 121. The electrical source may be any device or component operable to apply an electrical potential, which may, in embodiments, be a step potential. A detector 222 is disposed to detect a current at or downstream of a second electrode 122 in contact with a second point in or on the conductive system or medium. The detector may be any device or component operable to measure, estimate, or detect an electrical current. In embodiments, a computer 140 is provided and is disposed, adapted, and configured to compute an impedance property according to any of the methods disclosed herein. In embodiments the computer, controller, or other component is operably connected to one or more input or output devices, such as a keypad or display 143. In embodiments, there is provided a controller 224 adapted and configured to control the time at which the detector samples the current. In some embodiments the controller may control the time at which an electrical potential is applied to the upstream electrode 121. In some embodiments there are provided connections or interfaces for interfacing the controller with the electrical source, the detector, and/or the computer. In embodiments, a connection and/or interface 226 is provided for communicating a timing and/or other control signal from the controller to the detector, and/or communicating a measurement from the detector to the controller. In embodiments, a connection or interface 228 is provided for communicating a timing signal and/or other control signal from the controller to the electrical source. In embodiments, a connection or interface 230 is provided for communicating timing and/or other signals and/or data between the controller and the computer. In embodiments, a caliper 141 is provided for estimating a distance between points in or on the conductive system or medium, and there may be provided a connection and or interface between the caliper and the controller or computer for transmitting a control signal to the caliper and/or receiving a measurement from the caliper. It will be apparent that each of the disclosed components may be provided as one or more separate or discrete components, combined into one or more composite or integrated components, or provided in any other operable form or configuration.

Accordingly, disclosed herein is a method of estimating a measure of an electrical impedance property of at least one but less than all current-contributive conductive paths between a first point and a second point separated by a conductive medium offering at least two conductive paths of differing length between the points, the method including: applying an electrical potential at the first point at a time t0; making at least one measurement of the current at the second point at a time tS, wherein the ratio of the time interval (tS-t0) to the minimum time interval for an electromagnetic signal to propagate from the first point to the second point via the shortest conductive path is greater than one and less than the ratio of the length of the longest current-contributive conductive path to the length of the shortest conductive path; and using the at least one measurement of the current at the second point, estimating a measure of an electrical impedance property. In some embodiments, the electrical potential may include a step potential. In some embodiments, applying an electrical potential may include changing a potential already being applied, in which case making a measurement of the current may include making a measurement of the change in current due to the change in potential. In some embodiments, making a measurement of the current at the second point may include making a measurement at a point downstream of the second point, taking into account the size of the measuring instrument and/or the need to connect the measuring instrument to the second point via a lead or wire; in such cases, the lead, wire, and/or measuring instrument may be considered to be part of the conductive system and the point at which current is actually measured may be taken as the second point. In some embodiments, estimating a measure of an electrical impedance property may include estimating an impedance property of the shortest conductive path between the first point and the second point. In some embodiments, estimating a measure of an electrical impedance property may include estimating an impedance property of a composite path including the shortest conductive path between the first point and the second point. In some embodiments, the ratio of the time interval tS minus t0 to the minimum time interval for an electromagnetic signal to propagate from the first point to the second point via the shortest conductive path may be less than or equal to about 1.2. In some embodiments, the method may further include estimating the minimum time interval for an electromagnetic signal to propagate from the first point to the second point. In some embodiments, estimating the minimum time interval may include dividing the length of the shortest conductive path by the estimated speed of propagation of an electromagnetic signal in the conductive medium. In some embodiments, the method may include estimating the length of the shortest conductive path, which may include measuring or estimating the straight line distance between the first point and second point. In some embodiments, estimating the minimum time interval may include, after applying the electrical potential at the first point, observing the elapsed time before a signal attributable to the applied electrical potential is first detectable at the second point. In some embodiments, estimating a measure of an electrical impedance property may include: from the at least one measurement of the current at the second point, estimating the aggregate current passing from the first point to the second point along one or more but less than all current-contributive conductive paths from the first point to the second point. In some embodiments, the one or more but less than all current-contributive conductive paths from the first point to the second point may exclude any conductive path from the first point to the second point that is longer than 1.5 times the length of the shortest conductive path from the first point to the second point.

Also disclosed herein is a method of estimating a spatial distribution of a measure of an electrical impedance property within a conductive medium, including: according to any of the methods disclosed herein including those described in the preceding paragraph, estimating, for each of a plurality of non-identical pairs of points, where each pair of points includes a first point and a second point in or on the conductive medium, a measure of the electrical impedance contribution of at least one but less than all current-contributive conductive paths between the first point and second point of the pair; and combining the plurality of estimated measures to produce a representation of a spatial distribution of the impedance property. In some embodiments, the representation of a spatial distribution may include an image.

Also disclosed herein is an apparatus for estimating a measure of the electrical impedance contribution of at least one but less than all current-contributive conductive paths between a first point and a second point separated by a conductive medium offering at least two conductive paths of differing length between the points, including: a first electrode and a second electrode for making an electrical connection to the first point and second point, respectively; an electrical source for applying an electrical potential to the first electrode; a detector for making a measurement of the current at the second point; and a computer programmed to estimate a measure of an electrical impedance property from a measurement of the current at the second electrode obtained at a time $t_S$ subsequent to a time $t_0$ at which an electrical potential is applied to the first electrode, wherein the ratio of the time interval ($t_S$–t0) to the minimum time interval for an electromagnetic signal to propagate from the first point to the second point via the shortest conductive path is greater than one and less than the ratio of the length of the longest current-contributive conductive path to the length of the shortest conductive path. In embodiments, the apparatus may include a caliper for estimating the length of a shortest current path between the first point and second point. In embodiments, the apparatus may include a controller operatively connected to the detector and adapted and configured to control the detector to make a measurement of the current at the second electrode at a time tS relative to a time t0 at which an electrical potential is applied to the first electrode, wherein the ratio of the time interval (tS-t0) to the minimum time interval for an electromagnetic signal to propagate from the first point to the second point via the shortest conductive path is greater than one and less than the ratio of the length of the longest current-contributive conductive path to the length of the shortest conductive path.

Also disclosed herein is an apparatus for estimating a measure of an electrical impedance property of at least one but less than all current-contributive conductive paths between a first point and a second point separated by a conductive medium offering at least two conductive paths of differing length between the points, the apparatus including: means for performing the function of applying an electrical potential at the first point at a time t0; means for performing the function of making at least one measurement of the current at the second point at a time tS, wherein the ratio of the time interval (tS–t0) to the minimum time interval for an electromagnetic signal to propagate from the first point to the second point via the shortest conductive path is greater than one and less than the ratio of the length of the longest current-contributive conductive path to the length of the shortest conductive path; and means for performing the function of estimating a measure of an electrical impedance property using the at least one measurement of the current at the second point.

5. Other Embodiments

It will be noted that the methods described do not necessarily require that the path whose impedance properties are measured be a straight line path, as long as the path is the shortest conductive path between the electrodes. The number of paths selected for analysis is not limited to the number described in the examples or preferred embodiments herein, and is limited only by the computational resources available and the ability to make accurate current amplitude and phase measurements for a sufficient distribution of interrogation frequencies; the larger the number of paths, the better the resolution obtained, other factors being equal. The selection of interrogation frequencies is not limited to the ranges described in the examples and embodiments, and in principle any interrogation frequencies may be used provided that the wavelengths are not so short that the attenuation becomes too great for accurate measurement of currents. The interrogation signals are not necessarily limited to sinusoidal signals. Non-sinusoidal signals can be decomposed by Fourier analysis into a superposition of sinusoidal signals at specific frequencies in a manner well known to persons having ordinary skill in the art of signal processing. Such sinusoidal signals resulting from such decomposition can then be used to analyze the impedance properties of the object being imaged using the system and method described herein. It is therefore possible to apply a non-sinusoidal interrogation signal comprising a superposition of sinusoidal signals at two or more frequencies, measure the resulting current signal, decompose the current signal by Fourier methods into its component sinusoidal signals, and perform the analysis of impedance properties, using the system and method described herein, separately for each of the component sinusoidal signals. Although the interrogation signal is described in the examples and preferred embodiments herein as having a predetermined, fixed voltage amplitude, obviously the analysis can be carried out using a signal of fixed current amplitude and measuring the voltage signal produced, as will be apparent to a person having ordinary skill in the art of analyzing electrical signals. Although the examples and preferred embodiments discussed herein reflect the use of only two electrodes, it is possible to use an array of electrodes interrogated two at a time, provided that the straight line distance between electrode pairs is known or can be determined. Although the examples and preferred embodiments discussed herein reflect the supposition that the dimensions of the object, and therefore the straight line distances between electrodes, remains constant throughout the measurements, in the case of physiological measurements of regions such as the torso the dimensions may change due to breathing, movement, or for other reasons. It will be apparent upon inspection of the linear system describing the relationship between the measured currents and the path resistances and capacitances that it is merely necessary for the dimensions to remain constant during each single interrogation of a single electrode position pair at a single frequency, which can be accomplished nearly instantaneously. Although the examples and preferred embodiments discussed herein reflect the placement of electrodes on the outer surface of the object to be measured, the system and method described herein are equally applicable to configurations in which either electrode or both electrodes are placed at a point in the interior of the object. Doing so may make advisable the broadening of the range of assumed shunt path lengths, since the currents produced by the interrogation signals can then take less direct paths. Such configurations may be useful in geological applications where electrodes are placed in drilled holes, and in physiological measurement where electrodes are placed in the interior of the body by surgery, via a needle or catheter, produced by an implantable device, or otherwise.

It is not required that the signals used to interrogate the object be electrical signals; the system and method described herein is applicable to any type of signal characterized by wave-like propagation through an attenuating medium through which the signal tends to follow paths of least resistance, including, without limitation, acoustic signals.

It must be recognized that the measurements described herein may not necessarily provide exact straight line impedance values due to a variety of factors, not least of which is that a straight line has, by definition, infinitesimal thickness and therefore infinite impedance. The system and method discussed herein produces a reasonable measure related to the impedance along paths of finite thickness, corresponding to a resolution that can improved to an arbitrary extent by increasing the number of interrogation frequencies. The values produced by the methods described will, however, bear a relation to physiological properties, including impedance, and/or some composite thereof, and provide quantities that can usefully be employed to produce images that furnish information relevant to assessment of physiological states. Therefore, even to the extent that the values produced are not, strictly speaking, precisely accurate straight line impedance values, they can be used to produce images that themselves are useful.

B. Methods and Apparatus Relating to Estimation of a Measure of an Impedance Property From a Perturbation of the Conductivity State Another strategy for estimating an impedance property of a conductive system and/or conductive medium involves inducing a change affecting a conductivity or impedance property of at least one, but less than all, conductive paths. Consider a simple conductive system that has (or can be modeled as having) three conductive paths each having a resistance as illustrated in FIG. 1. If a known potential is applied across the electrodes 121 122, the resulting current may be measured, providing a reference measurement which will include the current due to all three paths. If a localized change is induced whereby one of the three conductive paths is blocked so that no current flows on the blocked path, the known potential may be applied and the current measured, providing a comparison measurement which will include the current flowing on only the two un-blocked paths. It follows from the superposition principle that the current attributable to the blocked path in the reference measurement can be obtained by subtracting the comparison measurement from the reference measurement.

The general principle just described can be used or adapted to estimate a measure of an electrical resistance or impedance property of any conductive medium offering any number of conductive paths between two points. The localized change need not necessarily achieve a complete blockage of current, nor need it be perfectly confined to a single conductive path. If the current blockage is only partial, it will nevertheless provide a measure of an impedance property that is reproducible (to the extent that the localized change is reasonably reproducible) and representative of a characteristic of the impedance distribution in the medium that can be used for imaging or any other application involving relations between impedance distribution and other properties of the medium, such as, for example, physiological properties of a biological medium. If the extent of the localized change is larger, so that the blockage affects more than one conductive path, then the resolution of the method may be reduced, but the difference in the measured signal between the reference measurement and the comparison measurement will nevertheless provide a useful measure of an impedance property characteristic of the impedance distribution in the conductive medium. The reference measurement and/or the comparison measurement need not necessarily be a measurement of current induced by an applied potential, but can, in an embodiment, include any measurement of a response of the conductive medium to an electrical signal applied thereto, wherein the measurement is of a quantity or property related to the electrical impedance or any component thereof. Thus, for example, a measurement could be of a potential in response to an applied current, or an applied signal could include an alternating current or potential at any frequency or combination of frequencies deemed useful in an application of interest.

Figure 11:
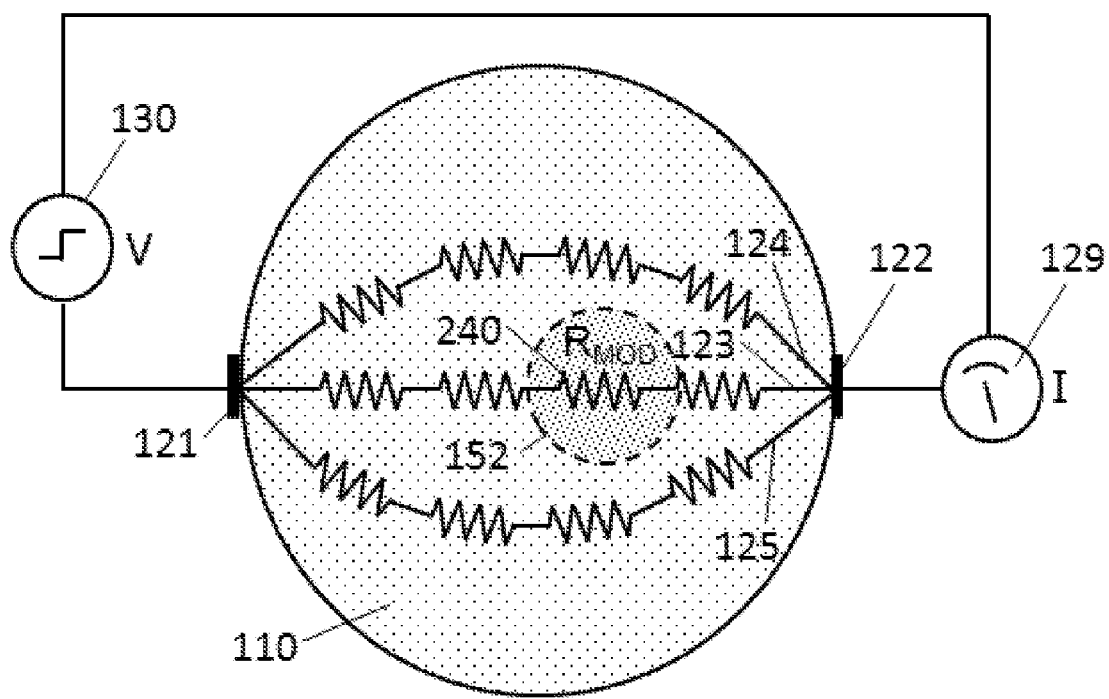
FIG. 11 illustrates an embodiment of a model of an effect of a localized change in conductivity.

A localized change need not necessarily produce a blockage or localized decrease in conductivity. In some embodiments, a localized change may include a change that produces a localized increase in conductivity affecting one or more but fewer than all conductive paths. Again consider a simplified model as depicted in FIG. 11A. As before, a reference measurement may be made by applying a known potential across the electrodes 121 122 and measuring the resulting current. A localized change may be induced to provide a comparison state, whereby the conductivity of a part 152 of one of the three conductive paths is increased, and the known potential may be applied and the current measured, again providing a comparison measurement. The difference between the reference measurement and the comparison measurement provides a measure of the magnitude and effect of the induced change in conductivity. For the simplified model of FIG. 11A, suppose that a localized change is induced in a localized region 152 whereby the value of the resistance $R_{MOD}$ 240 in the reference state is $R_{REF}$, and in the comparison state where the change has been induced, the value of the resistance $R_{MOD}$ is $R_{POST}$, where $R_{REF} > R_{POST}$. Since the parallel paths 124 125 are unchanged, the difference $\Delta I$ between the measured current $I_{REF}$ due to an applied potential V in the reference state and the measured current $I_{COMP}$ due to the applied potential V in the comparison state is due to the change in resistance of the path 123 affected by the localized change.

The total resistance of the affected path 123 in the comparison state is the sum of $R_{POST}$ plus the (series) resistance of the remainder of the path. Let the quantity $R_{FIXED}$ denote this sum. The total resistance of the affected path 123 in the reference state is the sum of $R_{FIXED}$ plus $\Delta R$, where $\Delta R$ is the difference $R_{REF} - R_{POST}$; in other words, $\Delta R$ is the change in the total resistance of the affected path. If the ratio $R_{POST}/\Delta R$ is known or can be estimated, then $R_{POST}$ can be computed from $\Delta I = (V/R_{POST}) - (V/(R_{POST} + \Delta R))$, which reduces to $R_{POST} = (V/(\Delta I\ (1 + (R_{POST}/\Delta R)))$. Since the (unaltered) path resistance $R_{REF} = R_{POST} + \Delta R$, $R_{REF}$ can be computed from $R_{POST}$ and the ratio $R_{POST}/\Delta R$. In embodiments, the ratio $R_{POST}/\Delta R$ may be estimated or measured in any manner that provides an estimated value of sufficient accuracy for an application of interest. For example, the ratio may be estimated by making a direct measurement of the ratio on a test model where a change is induced in a reproducible manner on a medium of similar composition wherein the localized region is isolated for measurement. In some embodiments the ratio may be estimated from the known characteristics of the induced change (which can, in embodiments, be determined or estimated by computational modeling, measurement on model systems, or using any other effective technique) and the extent of the localized region in comparison to the extent of the entire affected path. For example, if it can be determined or reasonably estimated that the induced change can be expected to reduce the resistance of the localized region to half its value, and if the localized region encompasses 10 percent of the affected path, then it could be estimated that the induced change will reduce the path resistance by 5 percent, so that the ratio $R_{POST}/\Delta R$ could be estimated to be 19.

More generally, a process of inducing a localized change from a reference state in a conductive medium or system, then making an electrical measurement on the system, when both the localized change and the measurement are accomplished in a uniform and reproducible manner (or in a manner that can be corrected or calibrated to enable valid comparisons), can be thought of as a way of interrogating the system with a spatially targeted perturbation, with the resulting measurement mapped to the locus at which the perturbation is applied. From a plurality of such interrogations and their associated loci, a spatial distribution and/or image can be obtained. In embodiments, it may be found useful to induce a localized change in a path that includes a straight line or other shortest conductive path between two points, so as to furnish information regarding an impedance property of the such path, since shortest path impedance properties, and especially straight line path impedance properties, lend themselves readily to construction of an image by familiar methods. Nevertheless, any spatially differentiated information on impedance properties can make a useful contribution to the determination of the spatial distribution of impedance properties and construction of images, by, for example, helping to exclude some of the possible distributions computed by other impedance imaging methods that (as is often the case) do not yield unique solutions.

Figure 7:
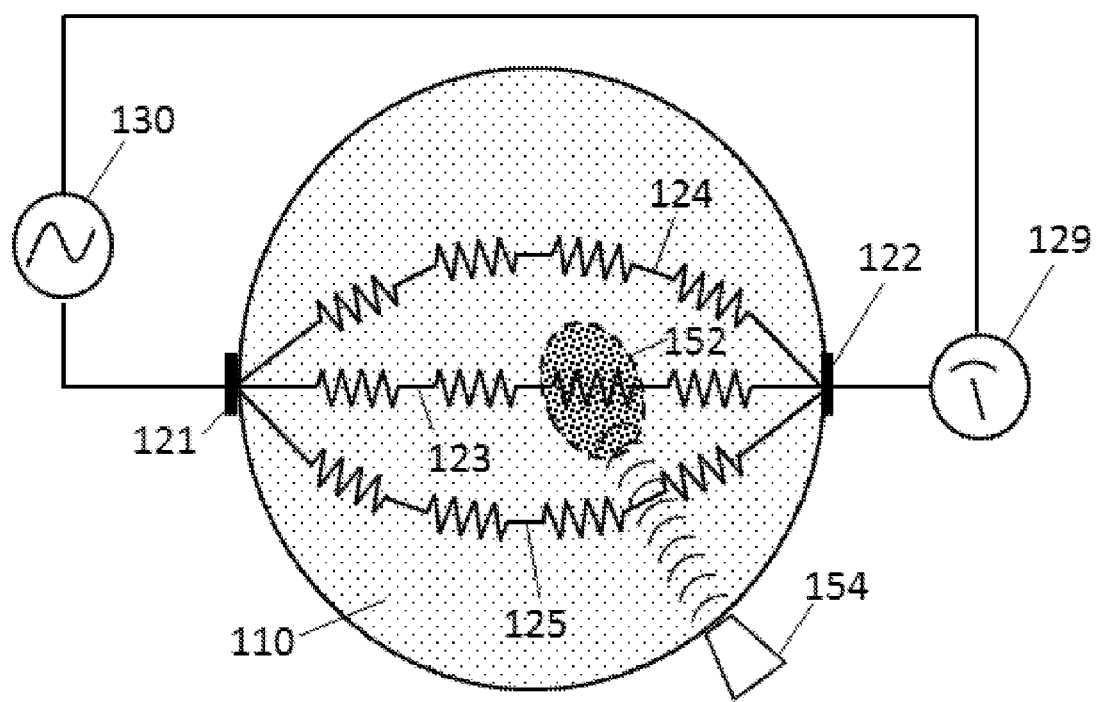
FIG. 7 illustrates schematically various aspects of an embodiment of a method and apparatus for estimating impedance properties in a conductive medium by altering a local state.

A localized change in a conductive medium may be induced in any manner operable to produce a change from a reference state in an electrical property of the medium, where the change in the property produces a detectable change in an electrical signal passing between two points in or on the conductive medium as compared to the reference state. For example, in a biological tissue, it is known that a locally applied mechanical pressure or stress will cause a localized change in the conductivity of the tissue, due at least in part to compression of the tissue squeezing out extracellular water. See, e.g., Keshtkar A. & Keshtkar A., Probe Pressure Optimization in Bio-impedance Spectroscopy, World Congress on Medical Physics and Biomedical Engineering, Sep. 7-12, 2009, Munich, Germany, IFMBE Proceedings Volume 25/7, 2009, pp. 78-80. Where a localized region of interest is directly accessible, such as, for example, via a catheter, mechanical pressure or stress can be applied by direct contact. Mechanical stress or pressure (and other potentially impedance-altering changes) can be applied in a localized region that is not accessible for direct contact by, for example, the use of high intensity focused ultrasound, with which a quite small area of focus can be achieved at arbitrary depth. Thus in embodiments as illustrated, for example, in FIG. 7, an ultrasound transducer 154 may be used to focus ultrasound energy in a localized region 152, thereby altering an impedance property of the localized region and of a conductive path 123 including the localized region, as compared to a reference state in which no ultrasound energy is applied. In some embodiments an ultrasound transducer may be made to scan its region of focus over a plurality of localized regions as a detector is made to measure a current or other signal in response to a potential or other signal between two points in or on the conductive medium, so that the measured signal (or a quantity derived from it) represents a rastering of a change in an impedance property in response to the applied localized ultrasound energy. In some embodiments the sampling of the electrical signal may be synchronized with a the ultrasonic perturbation, such as, for example, by synchronizing the sampling with the compression portion of the acoustic wave, or by causing sampling to occur at a determined interval following the application of an ultrasonic perturbation to a localized region. In embodiments, the duration and/or energy of the applied ultrasonic perturbation may be limited to a level well below a level at which ablation, undue heating, extended cavitation, or other tissue damage would occur.

Figure 8:
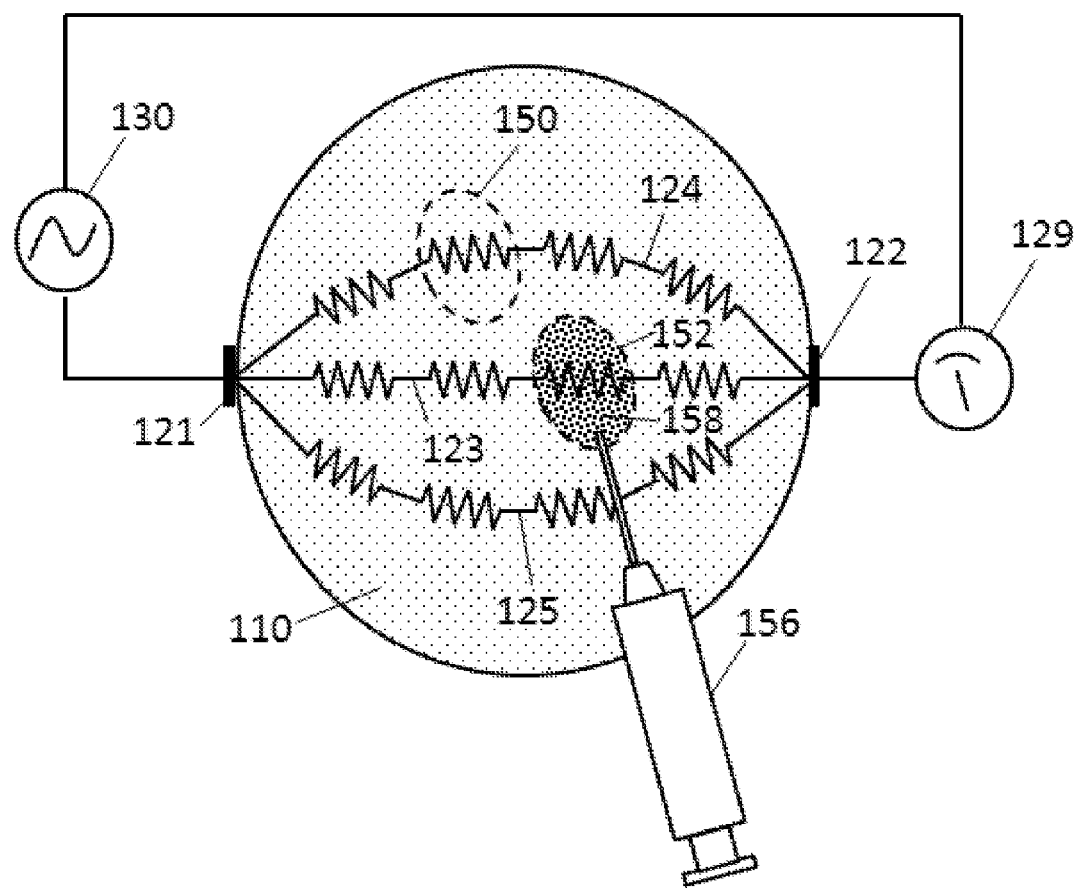
FIG. 8 illustrates schematically various aspects of an embodiment of a method and apparatus for estimating impedance properties in a conductive medium by introducing a sub stance.

For another example of inducing a localized change affecting an impedance property in a localized region, as illustrated in FIG. 8, a substance 158, having an impedance property differing from or capable of altering an impedance property of the medium in its reference state, may be introduced into a localized region to produce the comparison state. In various embodiments, a substance may be introduced in any manner operable to dispose the substance in the desired location, such as, for example, by a syringe and needle 156, by infusion through a catheter or cannula, or by any other delivery method. A substance may have any composition reasonably compatible with and preferably not destructive of the conductive medium, and capable of being introduced by the delivery method chosen. In various embodiments, for example, a substance may include a liquid having a low conductivity, such as, for example, an organic liquid, so that when infused at a localized region of a conductive medium the conductivity of the localized region is reduced, or may include a liquid having a high conductivity, such as, for example, an ionic liquid, so that when infused at a localized region of a conductive medium the conductivity of the localized region is increased, or may include a gas. In embodiments involving living biological tissue, an infused substance should preferably be biocompatible and should preferably be of a composition capable of being dissipated or metabolized so as to restore the reference state.

An apparatus may be provided for carrying out the methods disclosed herein, and may include any apparatus operable to apply an electrical potential between a first point and a second point separated by a conductive medium offering at least two conductive paths between the first point and second point, measure or estimate the current resulting therefrom, induce a localized change altering an impedance property of the conductive medium at a localized region, and compute, using the current values as measured or estimated with and without the localized change, a measure of a localized electrical impedance property of the conductive medium. In an embodiment, an apparatus may include an electrical source for applying an electrical potential. In an embodiment, an apparatus may include one or more electrodes for communicating an electrical potential from an electrical source to one or more loci in or on the conductive medium, and, where needed, transducing the electrical signal from an electronically propagated signal to an ionically propagated signal. In an embodiment, an apparatus may include an effector, which may include any device or component operable to induce a localized change affecting an impedance property of a localized region of a conductive medium. In embodiments, an effector may include an ultrasonic transducer adapted and configured to deliver a focused ultrasonic perturbation to a localized region of the conductive medium. In an embodiment, an effector may include a delivery component, which may include any device or component operable to deliver a substance to a localized region of a conductive medium, such as, for example, a syringe, cannula, catheter, capsule, or other carrier. In an embodiment, an apparatus may include a detector for detecting current at a locus in or on a conductive system. In an embodiment, an apparatus may include a controller for determining the sampling time at which the current is to be detected and controlling the detector to do so. In embodiments, the controller may determine the sampling time in whole or part by controlling or detecting the timing of the application of a localized change affecting an impedance property at a localized region of the conductive medium. In embodiments, a controller may optionally control the timing and/or other aspects of the application of an electrical potential at a locus, and/or may control the operation and/or timing of any other components of the apparatus. In embodiments, an apparatus may include a computer for computing or estimating a measure of an impedance property according to the methods disclosed herein, and may optionally include one or more interfaces and/or input or output devices for communicating data to and results from the computer.

Figure 12:
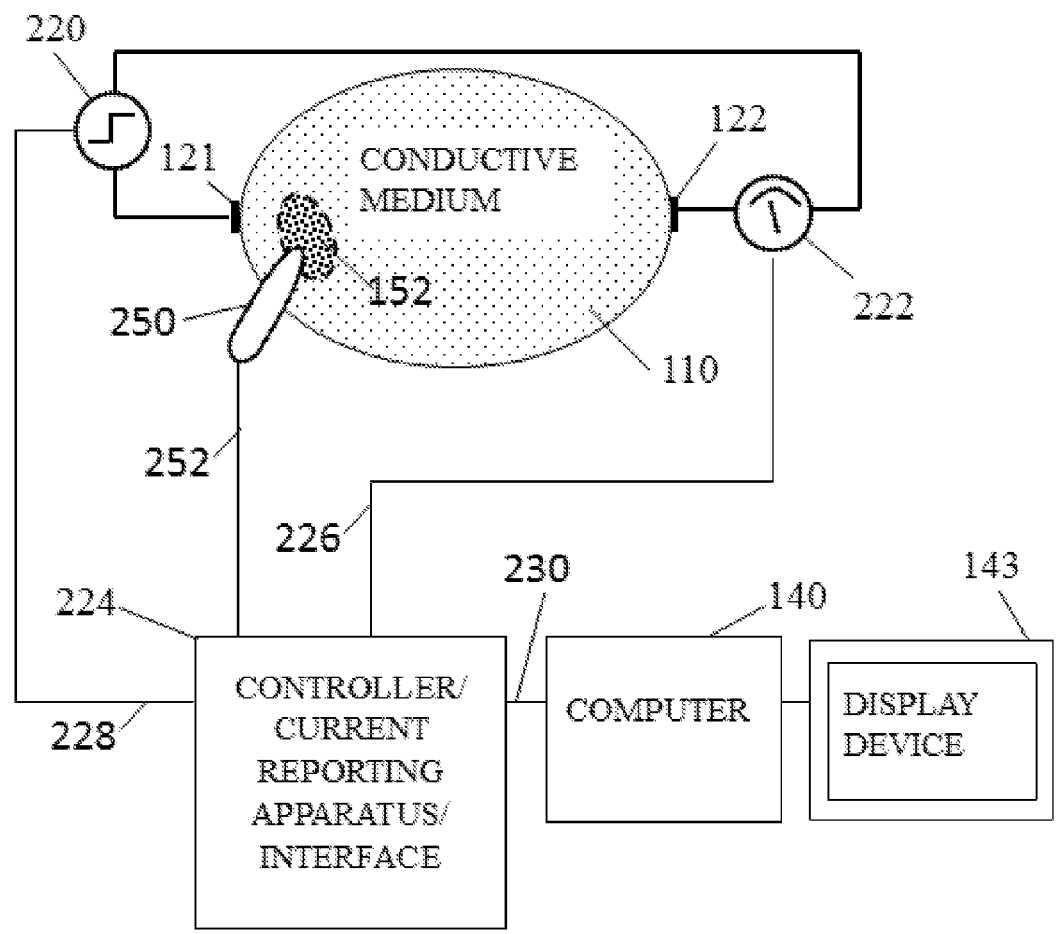
FIG. 12 illustrates an embodiment of an apparatus for measuring impedance related properties of an object.

FIG. 12 depicts an exemplary embodiment of an apparatus. An electrical source 220 is electrically connected to a point in or on a conductive system or medium 110 via an electrode 121. The electrical source may be any device or component operable to apply an electrical potential, which may, in embodiments, be a step potential, a fixed potential, an alternating potential of any frequency or combination of frequencies, and may have any amplitude, operable for inducing an electrical signal in the conductive medium. A detector 222 is disposed to detect a current at or downstream of a second electrode 122 in contact with a second point in or on the conductive system or medium. The detector may be any device or component operable to measure, estimate, or detect an electrical current. In embodiments, there is provided an effector 250 for inducing a localized change affecting an impedance property at a localized region 152 of the conductive medium. In embodiments, a computer 140 is provided and is disposed, adapted, and configured to compute an impedance property according to any of the methods disclosed herein. In embodiments the computer, controller, or other component is operably connected to one or more input or output devices, such as a keypad or display 143. In embodiments, there is provided a controller 224 which may be adapted and configured to control any or all of: the time at which the detector samples the current; one or more parameters determining the type of measurement made; the time at which an electrical potential is applied to the upstream electrode 121; one or more characteristics of the applied potential; and the operation and/or any parameter(s) of the effector. In some embodiments there are provided connections or interfaces for interfacing the controller with the electrical source, the detector, the effector, and/or the computer. In embodiments, a connection and/or interface 226 is provided for communicating a timing or other control signal from the controller to the detector, and/or communicating a measurement from the detector to the controller. In embodiments, a connection or interface 228 is provided for communicating a timing or other control signal from the controller to the electrical source. In embodiments, a connection or interface 230 is provided for communicating control signals and/or data between the controller and the computer. In embodiments, a connection or interface 252 is provided for communicating a timing or other control signal from the controller to the effector. It will be apparent that each of the disclosed components may be provided as one or more separate or discrete components, combined into one or more composite or integrated components, or provided in any other operable form or configuration.

Accordingly, there is provided a method of estimating a measure of a localized electrical impedance property of a conductive medium offering at least two conductive paths between a first point and second point, the method including: with the conductive medium in a reference impedance state, introducing an electrical signal between the first point and second point and making a reference measurement of a property of the electrical signal affected by passage through the conductive medium; inducing in the conductive medium a locally altered impedance state relative to the reference impedance state, wherein inducing a locally altered impedance state may include inducing a localized change in an electrical impedance property, wherein the localized change differentially affects an electrical impedance property of at least one conductive path relative to its effect on at least one other conductive path; with the conductive medium in the locally altered impedance state, introducing an electrical signal between the first point and second point and making a measurement of a property of the electrical signal affected by passage through the conductive medium; and comparing the reference measurement and the measurement made in the locally altered impedance state, and, using such comparison, estimating a measure of a localized electrical impedance property of the conductive medium.

In embodiments of a method of estimating a measure of a localized electrical impedance property, a localized change may differentially affect an electrical impedance property of at least one conductive path relative to its effect on at least one other conductive path by reducing the conductivity of at least one conductive path, or by increasing the conductivity of at least one conductive path. In some such embodiments, the at least one conductive path may include a shortest conductive path between the first point and second point. In some embodiments, a method of estimating a measure of a localized electrical impedance property may include associating the measure of the localized electrical impedance property of the conductive medium with the location within the conductive medium where the localized change in an electrical impedance property was induced.

In some embodiments, there is provided a method of determining a spatial distribution of a measure of an electrical impedance property within a conductive medium, including estimating a first measure of a localized electrical impedance property associated with a first location within the conductive medium, and estimating a second measure of a localized electrical impedance property associated with a second location within the conductive medium, wherein the second location is different from the first location. Each measure of a localized electrical impedance property may be estimated according to any of the methods disclosed herein.

In some embodiments, a method may include estimating a measure of a localized electrical impedance property of a conductive medium by any of the methods disclosed herein, and incorporating the measure in an image wherein the value of a measure of a localized electrical impedance property is depicted in association with its position within the conductive medium.

In some embodiments of a method of estimating a measure of a localized electrical impedance property, the measure of a localized electrical impedance property may be a measure of an impedance property of a path, which may comprise a shortest conductive path between the first point and the second point. In some embodiments there is provided a method of determining a spatial distribution of an impedance property within a conductive medium, including, according to any of the methods disclosed herein, estimating a measure of an impedance property of each of a plurality of paths each comprising a shortest conductive path between a different pair of points, and, from the measures of the impedance properties of the plurality of paths, computing a spatial distribution of a measure of an impedance property within the conductive medium. In some such embodiments a method may further include constructing an image depicting the spatial distribution of a measure of an impedance property within the conductive medium.

In some embodiments of a method of estimating a measure of a localized electrical impedance property of a conductive medium offering at least two conductive paths between a first point and second point, inducing a localized change in an electrical impedance property of the conductive medium may include directing an ultrasonic signal, such as by focused ultrasound, to a localized region of the conductive medium. In some such embodiments, a method may include directing focused ultrasound to two or more localized regions of the conductive medium while introducing an electrical signal between the first point and second point while making a measurement of a property of the electrical signal affected by passage through the conductive medium, and estimating from the measurement a measure of a localized electrical impedance property of the conductive medium associated with each of the two or more localized regions. In some embodiments, a measurement made in an altered impedance state may include a measurement synchronized with a portion of the waveform of the ultrasonic signal. In some embodiments, the ultrasonic signal may produce a standing wave in the localized region of the conductive medium.

In some embodiments of a method of estimating a measure of a localized electrical impedance property of a conductive medium, inducing a localized change in an electrical impedance property of the conductive medium includes introducing a substance into a localized region of the conductive medium. In some embodiments, introducing a substance into a localized region of the conductive medium may include introducing a gas into the localized region, and/or may include introducing an ionic substance into the localized region, and/or may include introducing into the localized region a low conductivity substance, and/or may include introducing into the localized region a high conductivity substance.

Also disclosed herein is an apparatus for estimating a measure of a localized electrical impedance property of a conductive medium offering at least two conductive paths between a first point and second point, which apparatus may include a signal generator for generating an electrical signal; a first electrode and a second electrode for applying an electrical signal between the first point and second point; a detector for measuring a property of the electrical signal affected by passage through the conductive medium; an effector for inducing in the conductive medium a localized change in the electrical impedance at a localized region of the conductive medium, wherein the localized change differentially affects the electrical impedance of at least one conductive path relative to the effect of the change on the electrical impedance of another conductive path; and a computer programmed to compare a measurement of a property of an electrical signal affected by passage through the conductive medium made when the conductive medium is in a reference impedance state and a measurement of a property of an electrical signal affected by passage through the conductive medium made when the conductive medium is in an altered impedance state resulting from a localized change in an electrical impedance property of the conductive medium, wherein the localized change differentially affects the electrical impedance of at least one conductive path relative to its effect on another conductive path, and using such comparison, to estimate a localized impedance property of the conductive medium. In embodiments, an effector may include an ultrasonic transducer for emitting ultrasonic waves, such as, for example, a focused ultrasound beam, into the localized region of the conductive medium. In some embodiments an ultrasonic transducer may be configured to produce an ultrasonic standing wave in a conductive medium. In some embodiments an effector may include a delivery component for introducing a substance into a localized region of the conductive medium.

Also provided is an apparatus for estimating a measure of a localized electrical impedance property of a conductive medium offering at least two conductive paths between a first point and second point, the apparatus including: means for performing the function of introducing an electrical signal between the first point and second point and making a reference measurement of a property of the electrical signal affected by passage through the conductive medium with the conductive medium in a reference impedance state; means for performing the function of inducing in the conductive medium a locally altered impedance state relative to the reference impedance state, wherein inducing a locally altered impedance state may include inducing a localized change in an electrical impedance property, wherein the localized change differentially affects an electrical impedance property of at least one conductive path relative to its effect on at least one other conductive path; means for performing the function of introducing an electrical signal between the first point and second point and making a measurement of a property of the electrical signal affected by passage through the conductive medium with the conductive medium in the locally altered impedance state; and means for performing the function of comparing the reference measurement and the measurement made in the locally altered impedance state and estimating a measure of a localized electrical impedance property of the conductive medium using such comparison.

C. Embodiments Relating to Measurement-Based Signatures and Classification Based Thereon It will be apparent that measurements and imaging of impedance-related properties of a conductive medium may vary considerably in accuracy, resolution, and/or correspondence to observable and/or inferable characteristics of the medium. While a commonly sought ideal might be (for example) high resolution spatial mappings of complex conductivity over a range of frequencies, in many applications the ultimate objective is not necessarily fine-grained determination of the impedance properties of the medium, but rather a conclusion about a condition of an entity, about which impedance information may contribute useful evidence. Thus for example, an ultimate goal might be to determine whether or not a pathological condition, such as, for example, a cancerous condition, is present in an organism. A high-resolution impedance image of a portion of the body of the organism might provide useful information, but making the desired diagnosis will typically require further analysis of the image and application of the informed judgment of an expert, taking into account known or assumed relationships between (for example) tissue impedance distributions and the presence or absence of the pathology of interest, and possibly taking into account other available evidence. In effect, the purpose of converting measurements to an image is to organize and present the information contained in the measurements in a manner comprehensible to a human expert—ideally, in a manner such that the portrayal makes the characteristics known or assumed to be relevant readily discernable.

It is typically the case, nevertheless, that the information content of an image is the same or (often) less than the information content of the measurements from which the image was derived. Thus, for example, an impedance image showing visually a region differing in appearance from expectation, at a locus where a pathology or other condition of interest is suspected, is easier to interpret than a list of impedance and other measurements from which the image was constructed, but the information content is not increased by processing the measurements into an image (unless information from other measurements is added in the process). And, the requirement to process the measurements into a human-comprehensible form imposes unnecessary constraints on what is essentially a classification problem—in this example, deciding whether or not a specified pathology or other condition is present. Further, by forcing the measurements through the filter of human assumptions regarding hypothesized relationships of the measurements to the classification decision, other potentially informative relationships may be discarded or overlooked. Thus, it is desirable to provide embodiments of systems and/or methods for employing electrical impedance-related measurements directly to inform classification decisions, by processing the measurements into a characteristic signature that can then be classified using a pattern recognition strategy. In effect, the signature may be thought of in conceptual terms as a kind of image in some arbitrary virtual space not comprehensible to humans, but in which, given appropriate feature selection, classifications of interest may be better demarcated and more readily obtained. A further advantage of the signature/pattern recognition approach is that the signature can easily be made to incorporate other unrelated information or evidence, so that the classification decision is informed not only by impedance-related measurements but also by any other available evidence bearing on the classification. Yet another advantage is that machine-executed pattern recognition strategies are often able to discern and classify patterns or regularities that would be unrecognizable to or overlooked by a human expert.

Disclosed herein are embodiments of systems and methods for classifying a condition of an entity, where the entity includes a conductive medium offering a plurality of conductive paths and an electrical or impedance-related characteristic of the conductive medium is potentially informative concerning the condition of interest. Examples of such entities may include physiological entities such as organisms and/or organs or other parts thereof; physical entities, such as geological formations, objects to be subjected to nondestructive testing, and/or other entities where direct measurement of interior properties is impractical or inconvenient; and any other entities presenting or capable of presenting a condition manifesting or correlating with a measurable electrical impedance-related property or combination thereof, of all or part of the conductive medium, and/or a change in such a property or combination of properties.

In embodiments, a condition may include any state, characteristic, or property of an entity capable of being classified or distinguished in any manner. Examples of conditions may include any pathological, physiological, anatomical, or other condition of an organism; any functional, structural, or other condition of an object; and any other condition or state of an entity that is distinguishable from at least one other condition or state of the entity. In embodiments, classifying a condition of an entity may include making any decision or estimate, by any method and/or in any form, regarding the whether the condition does or does not belong to a specific classification, including without limitation making an estimate of a probability that the condition does or does not belong to the specific classification, and/or making a determination or estimate of the degree or extent to which the condition belongs to the specific classification. Thus, in various embodiments, a classification may be binary—that is, classifying the condition entails a decision that the condition does or does not belong to one or more classifications; it may be probabilistic—that is, a probability measure may be assigned to the likelihood that the condition belongs to one or more classifications; and/or the range of possible classifications may be n-ary where n>2, or continuous.

Provided herein are embodiments of a method of classifying a condition of an entity, wherein the entity includes a plurality of points separated by a conductive medium offering a plurality of conductive paths between the points, by obtaining a plurality of impedance-interrogation measurements, processing the plurality of impedance-interrogation measurements into a signature, and estimating a classification of the condition by machine execution of a pattern recognition strategy. In embodiments, an impedance-interrogation measurement may be made by interrogating the conductive medium or the entity of which it is a part with an interrogation signal and making a measurement of a characteristic or quantity indicative of the response (which may include a null response) of the conductive medium and/or entity to the interrogation signal, wherein the characteristic or quantity measured is, or is capable of being, determined, affected, altered, or influenced in whole or part by any impedance property of the conductive medium and/or entity. In embodiments by way of further example, an impedance-interrogation measurement may include a measurement or estimate of a characteristic or property wherein the measurement includes at least one value obtained by applying or inducing an electrical signal at at least one point in or on a conductive medium or an entity of which it is a part, and thereupon measuring an electrical quantity. In embodiments, the electrical quantity may include any measurable or estimable quantity characteristic of or relating to an electrical state and affected or potentially affected in whole or part by any impedance property of the entity, and comprising a response (which may include a null response) to an interrogation signal. In embodiments, an electrical quantity may include, for example, an impedance value, a conductance value, a resistance value, a capacitance value, a reactance value, a current value, a voltage value, a frequency value, a phase shift value, a magnetic or electric field strength, or any combination, pattern, or function of any one or more such values. In embodiments, an interrogation signal may include any electrical signal of any amplitude, frequency, phase, wave shape, charge carrier(s), and having any other characteristics, reasonably compatible with the entity and capable of being applied to the conductive medium and/or entity or induced therein. Parts A and B of this disclosure include examples of signals that may be suitably employed, and various example impedance-interrogation measurements that may be made.

In embodiments of a method of classifying a condition of an entity, a plurality of impedance-interrogation measurements may be processed to produce a signature. In embodiments, a signature may include any data aggregation or data structure comprising a plurality of impedance-interrogation measurements and/or values derived therefrom, and having a form operable for comparison of one signature to another, such as, for example, a comparison of a feature vector or equivalent data structure, a pairwise dissimilarity representation, or a dissimilarity representation against a reference or standard signature of compatible construction. In embodiments, a signature should preferably be constructed such that each element of a signature is obtained in the same or a reasonably comparable way to the same element in another signature to which it is to be compared.

A simple example of an embodiment of a signature would be an n-dimensional vector of impedance-interrogation measurement values each taken at a specified locus in a specified manner, which could be represented as an ordered list of the n values. In embodiments, a signature may include one or more values derived from and/or obtained by combining impedance-interrogation measurement values, and/or values obtained from a function taking as arguments one or more impedance-interrogation measurement values and optionally any other inputs found useful for an application of interest. In many embodiments, values making up a signature may be numeric values, which may be continuous, discrete, limited to values selected from a set, or in any other operable form. Where useful, a value may also include any other data representation compatible with the pattern recognition strategy intended to be used, such as, for example, a boolean value, or a text or string value, or an aggregate value such as a complex number or vector.

As will be apparent to persons of skill in the art of pattern recognition, the performance of a signature-based pattern recognition system depends in part on the feature selection; that is, which features or values are chosen for inclusion in the feature vector or other signature representation, and what weighting, if any, is applied. In embodiments, feature selection may be performed by any of the many methods known to skilled artisans; for a simple example, pattern recognition may be performed using a plurality of different feature selections, the performance of the pattern recognizer may be measured, and the best-performing feature selection may be chosen. In some embodiments, feature selection may be optimized using any of the many optimization methods known to skilled artisans, such as, for example, genetic algorithms or regression analysis. In embodiments, the processing of features into signature values may include weighting of features and/or signature values according to their informational or evidentiary value as determined by any operable method of estimation.

In embodiments, classifying a condition of an entity may include determining or estimating a classification from a signature by machine execution of a pattern recognition strategy. In embodiments, a pattern recognition strategy may include any of the many strategies for classifying states or conditions represented by signatures known to persons of skill in the art of pattern recognition, including, for example, neural networks, genetic algorithms, evolutionary algorithms, deep learning algorithms, supervised machine learning, unsupervised machine learning, dimension reduction strategies, support vector machines, linear classifiers, binary tree classifiers, Gaussian process classifiers, k-nearest neighbor classifiers, Bayesian network classifiers, and comparison of one or more signatures against a reference or standard. It will be apparent that, although very simple pattern recognition can in some situations be carried out by hand calculations, and although visual or other comparisons by a human agent may in some settings be thought of as a kind of pattern recognition, effective pattern recognition of the kind contemplated herein entails a complexity and quantity of data manageable, as a practical matter, only by machine-executed processes; therefore "pattern recognition" as used herein refers to the machine-executed methods and techniques encompassed within the meaning of the term as ordinarily understood by persons of skill in the art.

By way of simple illustrative example, consider an entity upon which a predetermined set of n impedance-interrogation measurements have been made by applying predetermined signals at specified loci and measuring specified electrical quantities in a specified manner at other specified loci. The values determined by the impedance-interrogation measurements are processed into a sample signature consisting of an n-dimensional vector of the raw impedance-interrogation measurement values arranged in a predetermined order. The sample signature is compared against each of a positive and negative reference signature vector, obtained by making the same predetermined set of n impedance-interrogation measurements on, respectively, each of a positive reference entity known to belong to a classification of interest and a negative reference entity known not to belong to the classification of interest, and processing the measurements into positive and negative reference n-dimensional vectors in the same manner as for the sample signature vector. A measure of the distance between the sample signature vector and the positive reference signature vector may be computed, providing a measure of the similarity of the condition of the sample entity to the condition of the positive reference entity. A measure of the distance between the sample signature vector and the negative reference signature vector is computed, providing a measure of the similarity of the condition of the sample entity to the condition of the negative reference entity. The condition of the sample entity is then classified as positive with regard to the condition of interest if the computed distance of the sample signature vector from the positive reference signature vector is less than the computed distance of the sample signature vector from the negative reference signature vector; otherwise the condition of the sample entity is classified as negative.

The foregoing example suffices to illustrate that it is possible to make classification decisions based more or less directly on impedance-interrogation measurements and without the constraints implicit in the need to extract representations directly meaningful to humans. It will be apparent to persons of skill in the art that the foregoing example is relatively simplistic and crude, and that much better results may typically be obtained by employing more versatile methods of feature selection and processing of impedance-interrogation measurements into signatures, and by taking advantage of more sophisticated pattern recognition strategies, using all of the tools available to skilled artisans. The desirability of employing much larger training and/or reference sets will also be apparent. In a more preferred example, feature selection and processing are optimized using an appropriate strategy such as, for example, a genetic algorithm, to determine a feature set and, optionally, method of processing impedance-interrogation measurements into signature values; large training and test sets including signatures corresponding to known classifications are assembled; and a classifier such as, for example, a neural network or deep learning network, is trained on the training and test sets. Limited only or primarily by the sizes of the available training and test sets, the quality of the measurements, and the degree to which the selected features are informative, arbitrary classification accuracy may be obtained.

In embodiments, a signature may be augmented with values derived from sources other than impedance-interrogation measurements; any such values deemed informative may be used. Thus, for example, in an application where an entity is a living human organism and a diagnostic classification is desired, it may be found useful to augment the impedance-interrogation measurement-derived signature with additional values encompassing other information relevant to the diagnosis, such as, for example, one or more blood chemistry values; values derived from immunological testing; values derived from biopsy analysis; values derived from physiological testing; values derived from other imaging modalities such as, for example, x-ray, computed x-ray tomography, magnetic resonance, positron emission tomography, thermal, or ultrasound imaging; or values derived from other diagnostically relevant information sources. (In some embodiments, a signature does not comprise an image, in the sense of a graphical representation or visual depiction consistent with spatial reality, such as a bitmap image or vector graphic image; however, in some embodiments, data depicted in or obtained from such images may be used to augment a signature.) An advantage of the signature/pattern recognition strategy disclosed herein is that information from other sources may be readily incorporated in the signature and taken into account in making the classification, and if an appropriate feature selection strategy is employed, effective selection and weighting of informational inputs from a variety of sources can be arrived at in an automated fashion.

Figure 13:
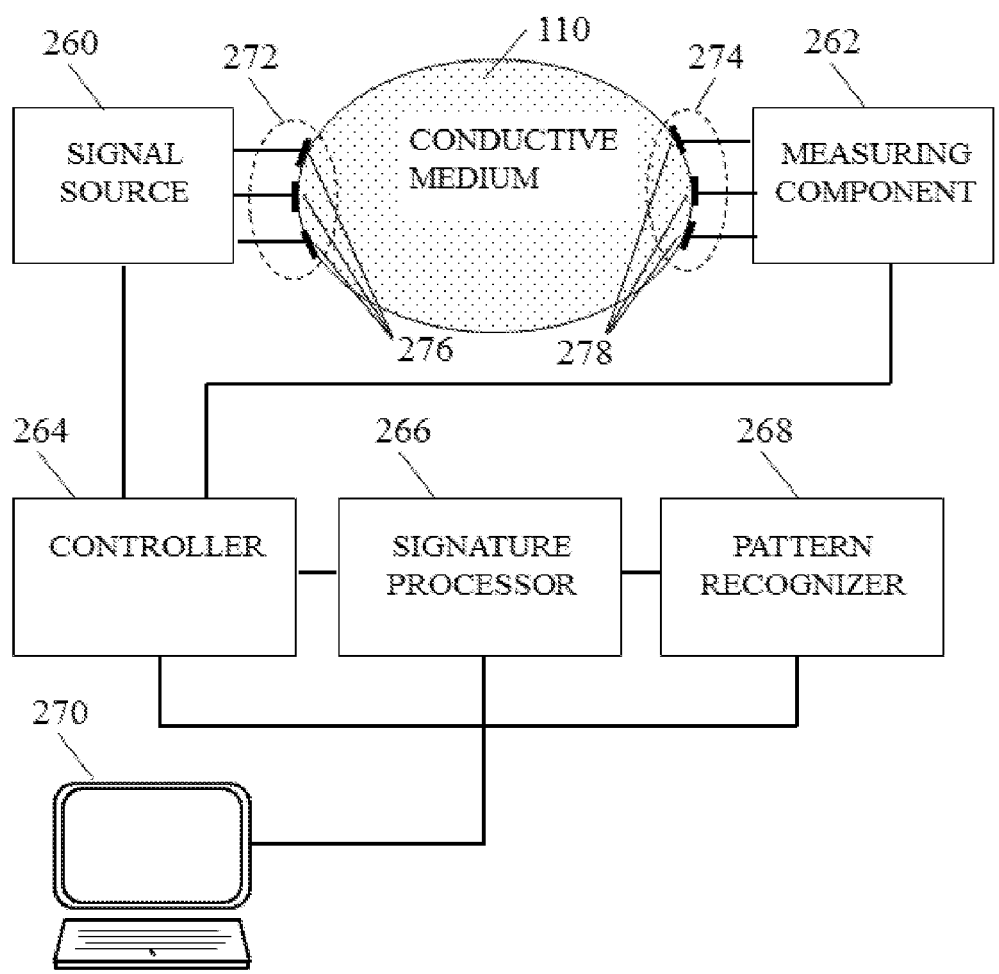
FIG. 13 illustrates an embodiment of a system for classifying a condition of an entity wherein the entity comprises a plurality of points separated by a conductive medium offering a plurality of conductive paths between the points.

Also provided herein are embodiments of a system for classifying a condition of an entity, wherein the entity includes a plurality of points separated by a conductive medium offering a plurality of conductive paths between the points. In an exemplary embodiment as depicted in FIG. 13 there is provided a signal source 260 for applying one or more electrical interrogation signals to one or more interrogation points 276 in or on a conductive medium 110, and a measuring component 262 for measuring or estimating at least one electrical quantity associated with each of a plurality of measurement points 278, wherein the conductive medium offers a plurality of conductive paths for a signal propagating from at least one of the interrogation points. Optionally an interrogation interface component 272 is provided for interfacing the signal source with the interrogation point(s) in or on the conductive medium. Optionally a measuring interface component 274 is provided for interfacing the measuring component with the measurement point(s) in or on the conductive medium. In an embodiment as depicted in FIG. 13 there may be provided a controller 264 adapted and configured to control the signal source and the measuring component to make a plurality of impedance-interrogation measurements, wherein each impedance-interrogation measurement comprises controlling the signal source to apply a signal at at least one interrogation point and thereupon controlling the measuring component to measure at least one electrical quantity from the conductive medium or the entity of which it is a part; a signature processor 266 adapted and configured to receive from the controller or from the measuring component a plurality of impedance-interrogation measurements and process the plurality of impedance-interrogation measurements into a signature; optionally, a pattern recognizer 268 adapted and configured to receive a signature from the signature processor and classify the signature by machine execution of a pattern recognition strategy; and optionally, a user interface 270 adapted and configured for receiving user input and transmitting it to the controller, signature processor, and/or pattern recognizer, and/or for receiving output from the controller, signature processor, and/or pattern recognizer and optionally communicating the output to a user and/or transmitting the output to another instrument or over a network.

In embodiments, a signal source may include any device or component or combination thereof operable to produce or emit an impedance-interrogation signal suitable for applying to a conductive medium in an application of interest, such as, for example, a signal generator, or a computer adapted and configured to produce a signal having the characteristics desired. In embodiments, a measuring component may include any device, component, instrument, or combination thereof operable to make or obtain measurements of electrical quantities for impedance-interrogation measurements appropriate for an application of interest, such as, for example, a voltage measuring instrument, a current measuring instrument, an oscilloscope, a signal amplifier, a signal averaging instrument, an analog-to-digital converter optionally coupled to a computer for reading and storing its output, and/or any other instrument operable for measuring an electrical quantity. In embodiments, an interrogation interface component may include any connector, transducer or other component operable for introducing a signal from the signal source into the conductive medium. In embodiments, a measuring interface component may include any connector, transducer or other component operable for detecting and/or transducing an electrical quantity desired to be measured. In embodiments, an interrogation interface component or a measuring interface component may optionally include one or more components for conditioning a signal, providing impedance matching and/or transduction between charge carrier types such as from electronic currents to ionic currents, amplification, and/or filtering, and may include an active or passive electrode or electrode array including compatible cabling.

In embodiments, a controller may include any device or component or combination thereof together with any interface, operable to control the functions of the signal source and measuring component so as to coordinate the measurement by the measuring component with the application of the signal by the signal source whereby the measuring component measures an electrical quantity in response to the interrogation signal applied by the signal source, and to receive, store, and transmit to the signature processor the values measured by the measuring component. Examples of controllers suitable for some embodiments include, for example, microcontrollers, computers, mobile devices such as smart phones or tablets, and/or any other devices programmable and/or configurable to perform the indicated functions. In embodiments, a signature processor may include any device or component or combination thereof operable to receive a plurality of impedance-interrogation measurement values, process them to derive a signature therefrom according to any method of representing a plurality of measurement values as a signature deemed useful in an application of interest, and report, output, and/or transmit the signature so derived, such as, for example, a computer, microcontroller, or other programmable and/or configurable device programmed and/or configured to perform the indicated functions. In embodiments, a pattern recognizer may include any device or component or combination thereof operable to receive a signature and classify the signature and/or a condition represented by the signature by machine execution of a pattern recognition strategy, such as a computer configured and/or programmed to receive one or more signatures and programmed, and optionally trained on and/or provided with suitable training or reference data, to execute a selected pattern recognition strategy compatible with the received signature(s). Typically the functions of one or more of a controller, signature processor, and pattern recognizer may be performed by one or more general purpose computers configured and/or programmed to perform the functions, but in an embodiment, a controller, signature processor, and/or pattern recognizer may also include one or more special purpose computers or other custom devices, together with suitable interfaces, configured and/or programmed to perform the indicated functions. More generally, it will be apparent that any one or more of the components of a system for classifying a condition of an entity as disclosed herein may, in embodiments, be combined or integrated into a single component, and that the functions performed by such components or combinations thereof may be subdivided in any other operable manner and their functions otherwise combined into one or more components in a manner different from that depicted in FIG. 13; the disclosure hereof extends to all such functionally equivalent combinations.

In embodiments, also provided herein is a method of classifying a condition of an entity having a plurality of points separated by a conductive medium offering a plurality of conductive paths between the points, the method including obtaining a plurality of impedance-interrogation measurements, processing the plurality of impedance-interrogation measurements into a signature, and from the signature, classifying a condition of the entity by machine execution of a pattern recognition strategy. In some embodiments of such a method, one or more of the impedance-interrogation measurement may include at least one value obtained by a method comprising applying an interrogation signal at at least one of the points and measuring an electrical quantity representing a response to the interrogation signal, wherein the response may include a null response; the entity may include a living organism and the conductive medium may include all or a portion of the living organism; classifying a condition of an entity may include classifying the condition of the entity as corresponding or not corresponding to a pathological state, or corresponding or not corresponding to a specific pathological state; applying an electrical signal may include inducing an ionic current in the conductive medium; the signature may be represented as a feature vector and optionally the pattern recognition strategy may include comparing the feature vector with at least one reference feature vector, and/or may include classifying the feature vector using a pattern recognizer trained on a training set of reference feature vectors; and/or at least one impedance-interrogation measurement may include an estimate of an impedance property of the conductive medium. In some embodiments of such a method, the signature may be represented as a feature vector and the pattern recognition strategy may include classifying the feature vector using a pattern recognition method selected from: a neural network, a genetic algorithm, an evolutionary algorithm, a deep learning algorithm, supervised machine learning, unsupervised machine learning, a dimension reduction strategy, a support vector machine, a linear classifier, a binary tree classifier, a Gaussian process classifier, a k-nearest neighbor classifier, and a Bayesian network classifier. In some such embodiments, at least one impedance-interrogation measurement includes an estimate of an impedance property of the conductive medium. In some such embodiments, the signature includes at least one value derived from a measurement or observation that is not an impedance-interrogation measurement. In some such embodiments, the plurality of impedance-interrogation measurements are not processed into a graphical representation or image. In some such embodiments, processing the plurality of impedance-interrogation measurements into a signature includes selecting a predetermined set of impedance-interrogation measurements or values derived therefrom for inclusion, and ordering the values in a predetermined manner. In some such embodiments, processing the plurality of impedance-interrogation measurements into a signature includes assigning weights to the values comprising the signature.

In some embodiments, a system for classifying a condition of an entity having a plurality of points separated by a conductive medium offering a plurality of conductive paths between the points may include a signal source for applying one or more electrical signals at one or more points, a measuring component for measuring one or more electrical properties of the entity, a controller adapted and configured to (a) control the signal source and the measuring component to make a plurality of impedance-interrogation measurements, and (b) produce an output comprising the values obtained from the plurality of impedance-interrogation measurements, and a signature processor adapted and configured to process the plurality of electrical properties into a signature. In some such embodiments, the system may further include a pattern recognizer programmed to classify, from the signature, a condition of the entity by machine execution of a pattern recognition strategy; a user interface component; and/or an interrogation interface component and/or a measuring interface component.

CONCLUDING MATTER

For clarity and to ensure completeness, certain of the aspects and/or embodiments disclosed herein may be overlapping in scope, described repetitively, or represent recitals of the same or equivalent elements or combinations expressed in alternative language. It will be apparent that the choice of particular phraseology and/or of particular aspects or elements to assert as claims involves many complex technical and legal considerations, and no inference should be drawn that alternative descriptions of a particular element or combination in this written description necessarily do or do not encompass different subject matter; except where context otherwise requires, each described aspect or element should be interpreted according to its own description.

It is intended that this specification be interpreted in accordance with the normal principles of English grammar and that words and phrases be given their ordinary English meaning as understood by persons of skill in the pertinent arts except as otherwise explicitly stated. If a word, term, or phrase is intended to be further characterized, specified, or narrowed in some way, then additional adjectives, modifiers, or descriptive text have been included in accordance with the normal principles of English grammar. It is intended that the meanings of words, terms, or phrases should not be modified or characterized in a manner differing from their ordinary English meaning as understood by persons of skill in the relevant arts except on the basis of adjectives, modifiers, or descriptive text that is explicitly present.

Except as otherwise explicitly stated, terms used in this specification, including terms used in the claims and drawings, are intended as "open" terms. That is, for example, the words "including" and "comprising" should be interpreted to mean "including but not limited to," the word "having" should be interpreted to mean "having at least," the word "includes" should be interpreted to mean "includes but is not limited to," the phrases "for example" or "including by way of example" should be interpreted as signifying that the example(s) given are non-exhaustive and other examples could be given, and other similar words and phrases should be given similar non-exclusive meanings. Except as explicitly stated, ordinals used as adjectives (e.g. "first object", "second object", etc.) in this specification, including claims and drawing figures, are intended merely to differentiate and do not imply that any particular ordering is required. Thus, for example, unless otherwise explicitly stated, "first measurement" and "second measurement" do not imply that the first measurement necessarily takes place before the second measurement, but merely that they are distinct measurements.

In the written description and appended claims, the indefinite articles "a" and/or "an" are intended to mean "at least one" or "one or more" except where expressly stated otherwise or where the enabling disclosure requires otherwise. The word "or" as used herein is intended to mean "and/or", except where it is expressly accompanied by the word "either", as in "either A or B". Applicants are aware of the provisions of 35 U.S.C. § 112, ¶6. The use of the words "function," "means" or "step" in the written description, drawings, or claims herein is not intended to invoke the provisions of 35 U.S.C. § 112, ¶6, to define the invention. To the contrary, if the provisions of 35 U.S.C. § 112, ¶6 are sought to be invoked, the claims will expressly include one of the exact phrases "means for performing the function of" or "step for performing the function of". Moreover, even if the provisions of 35 U.S.C. § 112, ¶6 are explicitly invoked to define a claimed invention, it is intended that the claims not be limited only to the specific structure, material or acts that are described in the preferred embodiments, but in addition, extend to any and all structures, materials or acts that perform the claimed function as described in alternative embodiments or forms of the invention, or that are well known present or later-developed equivalent structures, material or acts for performing the claimed function.

Any of the methods of the present disclosure may be implemented in whole or part in hardware, software, or both, or by a computer program, and may be carried out using any of the disclosed devices or apparatus according to any aspect or embodiment of the present invention, or in any other operable manner.

In the foregoing description, various details, specific aspects, embodiments, and examples have been described in order to illustrate and explain the subject matter, to provide a thorough understanding of the various aspects, to enable persons skilled in the pertinent arts to practice the described subject matter, and to disclose the best mode of doing so known to applicants. These details, specific aspects, embodiments, and examples are not intended to be limiting; rather, it will be apparent to persons of skill in the relevant arts that, based upon the teachings herein, various changes, substitutions, modifications, rearrangements, may be made and various aspects, components, or steps may be omitted or added, without departing from the subject matter described herein and its broader aspects. Except as otherwise expressly stated or where aspects or features are inherently mutually exclusive, aspects and features of any embodiment described herein may be combined with aspects and features of any one or more other embodiments. Titles, headings, and subheadings herein are intended merely as a convenience for locating content, and do not limit or otherwise affect the interpretation of the content of the disclosure. The appended claims are intended to encompass within their scope any and all changes, substitutions, modifications, rearrangements, combinations of aspects or features, additions, and omissions that are within the spirit and scope of the subject matter as described herein and/or within the knowledge of a person of skill in the art. The scope of the invention is defined by the claims, and is not limited by or to the particular embodiments or aspects chosen for detailed exposition in the foregoing description, but rather extends to all embodiments or aspects as defined by the claims, as well as any equivalents of such embodiments or aspects, whether currently known or developed in the future.

I claim:

1. A system for classifying a condition of an entity comprising a plurality of points separated by a conductive medium offering a plurality of conductive paths between the points, the system comprising:
    a signal source for applying one or more electrical signals at one or more points;
    a measuring component for measuring one or more electrical properties of the entity;
    an interface for receiving at least one informative value from a source external to the system;
    a controller adapted and configured to (a) control the signal source and the measuring component to make a plurality of impedance-interrogation measurements, (b) produce an output comprising the values obtained from the plurality of impedance-interrogation measurements; and (c) receive from the interface at least one informative value from a source external to the system;
    a signature processor adapted and configured to process the plurality of impedance-interrogation measurements and the at least one informative value from a source external to the system into a signature; and
    a pattern recognizer programmed to classify, from the signature, a condition of the entity by machine execution of a pattern recognition strategy.

2. The system of claim 1, wherein each impedance-interrogation measurement comprises at least one value obtained by a method comprising applying an interrogation signal at at least one of the points and measuring an electrical quantity comprising a response to the interrogation signal, wherein the response may comprise a null response.

3. The system of claim 1, wherein the entity comprises a living organism and the conductive medium comprises all or a portion of the living organism.

4. The system of claim 1, wherein classifying a condition of an entity comprises classifying the condition of the entity as corresponding or not corresponding to a pathological state.

5. The system of claim 1, wherein classifying a condition of an entity comprises classifying the condition of the entity as corresponding or not corresponding to a specific pathological state.

6. The system of claim 1, wherein applying an electrical signal comprises inducing an ionic current in the conductive medium.

7. The system of claim 1, wherein the signature comprises a feature vector.

8. The system of claim 1, wherein the signature comprises a feature vector and the pattern recognition strategy comprises comparing said feature vector with at least one reference feature vector.

9. The system of claim 1, wherein the signature comprises a feature vector and the pattern recognition strategy comprises classifying the feature vector using a pattern recognizer trained on a training set of reference feature vectors.

10. The system of claim 1, wherein the signature comprises a feature vector and the pattern recognition strategy comprises classifying the feature vector using a pattern recognition method selected from: a neural network, a genetic algorithm, an evolutionary algorithm, a deep learning algorithm, a supervised machine learning algorithm, an unsupervised machine learning algorithm, a dimension reduction strategy, a support vector machine, a linear classifier, a binary tree classifier, a Gaussian process classifier, a k-nearest neighbor classifier, and a Bayesian network classifier.

11. The system of claim 1, wherein at least one impedance-interrogation measurement comprises an estimate of an impedance property of the conductive medium.

12. The system of claim 1, wherein the at least one informative value from a source external to the system is not a value obtained from an impedance-interrogation measurement.

13. The system of claim 1, wherein the plurality of impedance-interrogation measurements are not processed into a graphical representation or image.

14. The system of claim 1, wherein processing the plurality of impedance-interrogation measurements and the at least one informative value from a source external to the system into a signature comprises selecting a predetermined set of impedance-interrogation measurements or values derived therefrom for inclusion, and ordering the measurements or values and the at least one informative value in a predetermined manner.

15. The system of claim 1, wherein processing the plurality of impedance-interrogation measurements into a signature comprises assigning weights to the values comprising the signature.

16. The system of claim 1, wherein the interface for receiving at least one informative value from a source external to the system comprises a user interface adapted and configured for entry of the at least one informative value by a user.

17. The system of claim 1, wherein the at least one informative value from a source external to the system comprises non-numeric data.

18. The system of claim 1, wherein the at least one informative value from a source external to the system comprises textual data.

19. The system of claim 1, wherein the at least one informative value from a source external to the system comprises an image.

20. The system of claim 1, wherein the at least one informative value from a source external to the system is not a sensor output.

* * * * *